US007488792B2

(12) United States Patent
Ruoslahti et al.

(10) Patent No.: US 7,488,792 B2
(45) Date of Patent: Feb. 10, 2009

(54) COLLAGEN-BINDING MOLECULES THAT SELECTIVELY HOME TO TUMOR VASCULATURE AND METHODS OF USING SAME

(75) Inventors: Erkki Ruoslahti, Rancho Santa Fe, CA (US); Markus Essler, München (DE); Darren M. Brown, San Diego, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 0 days.

(21) Appl. No.: 10/648,813

(22) Filed: Aug. 25, 2003

(65) Prior Publication Data

US 2005/0048063 A1 Mar. 3, 2005

Related U.S. Application Data

(60) Provisional application No. 60/509,048, filed on Aug. 28, 2002.

(51) Int. Cl.
*C07K 5/00* (2006.01)
*C07K 7/06* (2006.01)

(52) U.S. Cl. .................. 530/300; 530/350; 530/328; 530/327; 530/326

(58) Field of Classification Search ................ 530/300, 530/350; 435/7.1
See application file for complete search history.

(56) References Cited

U.S. PATENT DOCUMENTS

| 5,320,970 | A | 6/1994 | Eyre et al. | |
| 5,541,295 | A | 7/1996 | Barrach et al. | |
| 5,622,699 | A | 4/1997 | Ruoslahti et al. | 424/93.6 |
| 5,763,272 | A | 6/1998 | Naser et al. | |
| 5,874,399 | A * | 2/1999 | Samal | 514/2 |
| 6,030,792 | A | 2/2000 | Otterness et al. | |
| 6,132,976 | A | 10/2000 | Poole et al. | |
| 6,491,894 | B1 * | 12/2002 | Ruoslahti et al. | 424/9.1 |
| 2003/0113331 | A1 | 6/2003 | Brooks et al. | |
| 2004/0091482 | A9 | 5/2004 | Watkins et al. | |

FOREIGN PATENT DOCUMENTS

| EP | 0 510 949 A2 | 10/1992 |
| EP | 0 921 395 A2 | 12/1998 |
| WO | WO 94/14070 A1 | 6/1994 |
| WO | WO 95/04282 A1 | 2/1995 |
| WO | WO 97/44059 A2 | 11/1997 |
| WO | WO 98/10795 | 3/1998 |
| WO | WO 98/35235 A1 | 8/1998 |
| WO | WO 99/06840 A1 | 2/1999 |
| WO | WO 99/13329 | 3/1999 |
| WO | WO 99/46284 | 9/1999 |
| WO | WO 00/40597 | 7/2000 |

OTHER PUBLICATIONS

Mathews and Van Holde, Biochemistry, 1996, pp. 165-171.*
W. Burgess, AShaheen, et al., Activities of Heparin-binding (Acidic Fibroblast) Growth Factor-1 from its Receptor-binding Activities by Site-directed Mutagenesis of a Single Lysine Residue. The Journal of Cell Biology. Vo. 111, 1990, 2129-2138.*
Lazar et al., Molecular and Cellular Biology, vol. 8, p. 1247-1252, 1988.*
Simth et al., (Chem Rev, vol. 97, pp. 391-410).*
Antman, "Randomized Trials of High Dose Chemotherapy for Breast Cancer," *Biochimica et Biophysica Acta* 1471:M89-M98 (2001).
Arap et al., "Cancer Treatment by Targeted Drug Delivery to Tumor Vasculature in a Mouse Model," *Science* 279:377-380 (1998).
Borgstrom et al., "Importance of VEGF for breast cancer angiogenesis in vivo: implications from intravital microscopy of combination treatments with an anti-VEGF neutralizing monoclonal antibody and doxorubicin," *Anticancer Res.* 19:4203-4214 (1999).
Brown et al., "A novel approach for the identification of unique tumor vasculature binding peptides using an *E. coli* peptide display library," *Ann. Surg. Oncol.* 7:743-749 (2000).
Burris III, "Docetaxel (Taxotere) Plus Trastuzumab (Herceptin) in Breast Cancer," *Semin. Oncol.* 28 (suppl 3) :38-44 (2001).
Carnemolla et al., "Enhancement of the antitumor propeties of interleukin-2 by its targeted delivery to the tumor blood vessel extracellular matrix," *Blood* 99:1659-1665 (2002).
Chan et al., "Prospective Randomized Trial of Docetaxel Versus Doxorubicin in Patients with Metastatic Breast Cancer," *J. Clin. Oncol.* 17:2341-2354 (1999).
Chen et al., "RGD-Tachyplesin Inhibits Tumor Growth," *Cancer Res.* 61:2434-2438 (2001).
Crown, "The Platinum Agents: A Role in Breast Cancer Treatment?," *Semin. Oncol.* 28 (suppl 3) :28-37 (2001).
Curnis et al., "Enhancement of tumor necrosis factor alpha antitumor immunotherapeutic properties by targeted delivery to aminopeptides N (CD 13)," *Nature Biotech.* 18:1185-1190 (2000).
Dogic et al., "Extracellular matrix, integrins and focal adhesions," *Curr. Topics Pathol.* 93:75-83 (1999).
Ellerby et al., "Anti-cancer activity of targeted pro-apoptotic peptides," *Nat. Med.* 5:1032-1038 (1999).
Engvall et al., "Nonhelical, fibronectin-binding basement-membrane collagen from endodermal cell culture," *Cell* 29:475-482 (1982).
Essler and Ruoslahti, "Molecular specialization of breast vasculature: A breast-homing phage-displayed peptide binds to aminopeptidase P in breast vasculature," *Proc. Natl. Acad. Sci. USA* 99:2252-2257 (2002).

(Continued)

*Primary Examiner*—Larry R. Helms
*Assistant Examiner*—Lei Yao
(74) *Attorney, Agent, or Firm*—McDermott Will & Emery LLP

(57) ABSTRACT

The present invention provides a conjugate containing a therapeutic agent linked to a homing molecule that selectively homes to tumor vasculature and selectively binds collagen such as non-helical collagen or collagen IV. In one embodiment, the conjugate contains a homing peptide or peptidomimetic that includes the amino acid sequence CREKA (SEQ ID NO: 1) or a conservative variant or peptidomimetic thereof.

93 Claims, 11 Drawing Sheets

OTHER PUBLICATIONS

Fisher et al., "Tamoxifen for Prevention of Breast Cancer: Report of the National Surgical Adjuvant Breast and Bowel Project P-1 Study," *J. Natl. Cancer Instit.* 90:1371-1388 (1998).

Harris et al., "Cancer of the Breast", *Cancer: Principles and Practice of Oncology*, 4th Edition, Chapter 40, DeVita, Jr. et al., J.P. Lippincott: Philadelphia (1993).

Herbst et al., "Differential effects of laminin, intact type IV collagen, and specific domains of type IV collagen on endothelial cell adhesion and migration," *J. Cell Biol.* 106:1365-1373 (1988).

Hood et al., "Tumor regression by targeted gene delivery to the neovasculature," *Science* 296:2904-2407 (2002).

Hoppe and Reid, "Collectins—soluble proteins containing collagenous regions and lectin domains—and their roles in innate immunity," *Protein. Sci.* 3:1143-1158 (1994).

Jenkins and Raines, "Insights on the conformational stability of collagen," *Nat. Prod. Rep.* 19:49-59 (2002).

Kennel et al., "Labeling and distribution of linear peptides identified using in vivo phage-display selection for tumors," *Nuc. Med. Biol.* 27:815-825 (2000).

Koivunen et al., "Tumor Targeting with a Selective Gelatinase Inhibitor," *Nat. Biotechnol.* 17:768-774 (1999).

Kühn, "Basement membrane (Type IV) collagen," *Matrix Biology* 14:439-445 (1994).

Laakkonen et al., "A tumor-homing peptide with a targeting specificity related to lymphatic vessels," *Nature Med.* 8:751-755 (2002).

Marneros and Olsen, "The role of collagen-derived proteolytic fragments in angiogenesis," *Matrix Biology* 20:337-345 (2001).

Myllyharju and Kivirikko, "Collagens and collagen-related diseases," *Ann. Med.* 33:7 (2001).

Oku et al., "Anti-neo-vascular therapy using novel peptides homing to angiogenic vessels," *Oncogene* 21:2662-2669 (2002).

Paridaens et al., "Paclitsxel Versus Doxorubicin as First-Line Single-Agent Chemotherapy for Metastatic Breast Cancer: a European Organization for Research and Treatment of Cancer Randomized Study with Cross-over," *J. Clin. Oncol.* 18:724-733 (2000).

Pasqualini and Ruoslahti, "Organ Targeting in Vivo Using Phage Display Peptide Libraries," *Nature* 380:364-366 (1996).

Porkka et al., "A fragment of the HMGN2 protein homes to the nuclei of tumor cells and tumor endothelial cells in vivo," *Proc. Natl. Acad. Sci. USA* 99:7444-7449 (2002).

Rajotte et al., "Molecular Heterogeneity of the Vascular Endothelium Revealed by in Vivo Phage Display," *J. Clin. Invest.* 102:430-437 (1998).

Rasmussen et al., "Tumor cell targeting by phage-displayed peptides," *Cancer Gene Ther.* 9:606-612 (2002).

Ritter et al., "Insulin-like growth factor 2 and potential regulators of hemangioma growth and involution identified by large-scale expression analysis," *Proc. Natl. Acad. Sci. USA* 99:7455-7460 (2002).

Ruoslahti and Rajotte, "An address system in the vasculature of normal tissues and tumors," *Annu. Rev. Immunol.* 18:813-827 (2000).

Sado et al., "Organization and expression of basement membrane collagen IV genes and their roles in human disorders," *J. Biochem.* 123:767-776 (1998).

Sidhu et al., "Phage display for selection of novel binding peptides," *Methods Enzym.* 328:333-363 (2000).

Sipkins et al., "Detection of tumor angiogenesis in vivo by αVβ3-targeted magnetic resonance imaging," *Nature Med.* 4:623-626 (1998).

Timpl and Brown, "Supramolecular assembly of basement membranes," *Bioessays* 18:123-132 (1996).

Timpl et al., "Macromolecular organization of basement membranes," *Curr. Opin. Cell Biol.* 8:618-624 (1996).

Tsai, "Stuck on the ECM," *Trends Cell Biol.* 8:292-295 (1998).

Vicini et al., "Accelerated Treatment of Breast Cancer," *Journal of Clinical Oncology* 19:1993-2001 (2001).

White et al., "Antibody-Targeted Immunotherapy for Treatment of Malignancy," *Annu. Rev. Med.* 52:125-145 (2001).

Wolff, "Systemic Therapy," *Curr. Opin. Oncology* 12:532-540 (2000).

Xu et al., "Proteolytic exposure of a cryptic site within collagen type IV is required for angiogenesis and tumor growth in vivo," *J. Cell Biol.* 154:1069-1079 (2001).

Yoshikawa et al., "Secretion of non-helical collagenous polypeptides of α1 (IV) and α2 (IV) chains upon depletion of ascorbate by cultured human cells," *J. Biochem.* 129:929-936 (2001).

GenBank Accession No. XP_159359.

GenBank Accession No. XP_166493.

GenBank Accession No. NP_493955.

Bellon, "Quantification and specific detection of collagenous proteins using an enzyme-linked immunosorbent assay and an immunoblotting for cyanogen bromide peptides," *Analytical Biochemistry* 150, 188-202 (1985).

Borza et al., "The Goodpasture Autoantigen," *J. Biol. Chem.* 275(8):6030-6037 (2000).

David et al., "Hydrophobic amino acid residues are critical for the immunodominant epitope of the Goodpasture autoantigen," *J. Biol. Chem.* 276(9):6370-6377 (2001).

Kalluri et al., "Specificity of circulating and tissue-bound autoantibodies in Goodpasture Syndrome," *Pro. Assoc. Am. Physicians* 108(2)134-139 (1996).

Nakanishi et al., "Immunohistochemical study of α1-5 chanins of type IV collagen in hereditary nephritis," *Kid. Inter.* 46:1413-1421 (1994).

Timpl, "Antibodies to collagens and procollagens," *Methods in Enzymology* 82:472-498 (1982).

Wheatcroft et al., "Evidence of in situ stability of the type IV collagen triple helix in human inflammatory bowel disease using a denaturation of specific epitope antibody," *Matrix Biology* 18:361-372 (1999).

Wick et al., "Characterization of antibodies to basement membrane (type iv) collagen in immunohistological studies," *Immunobiol*, 156:372-381 (1979).

Xu et al., "Generation of monoclonal antibodies to cryptic collagen sites by using subtractive immunization," *Hybridoma*, 19(5): 375-385 (2000).

Xu et al., "Proteolytic exposure of a cryptic site within collagen type IV is required for angiogenesis and tumor growth in vivo," *J. Cell Biol.*, 154(5):1069-1079 (2001).

Yoshioka et al., "Type IV collagen α5 chain," *Am. J. Path.* 144(5)986-996 (1994).

* cited by examiner

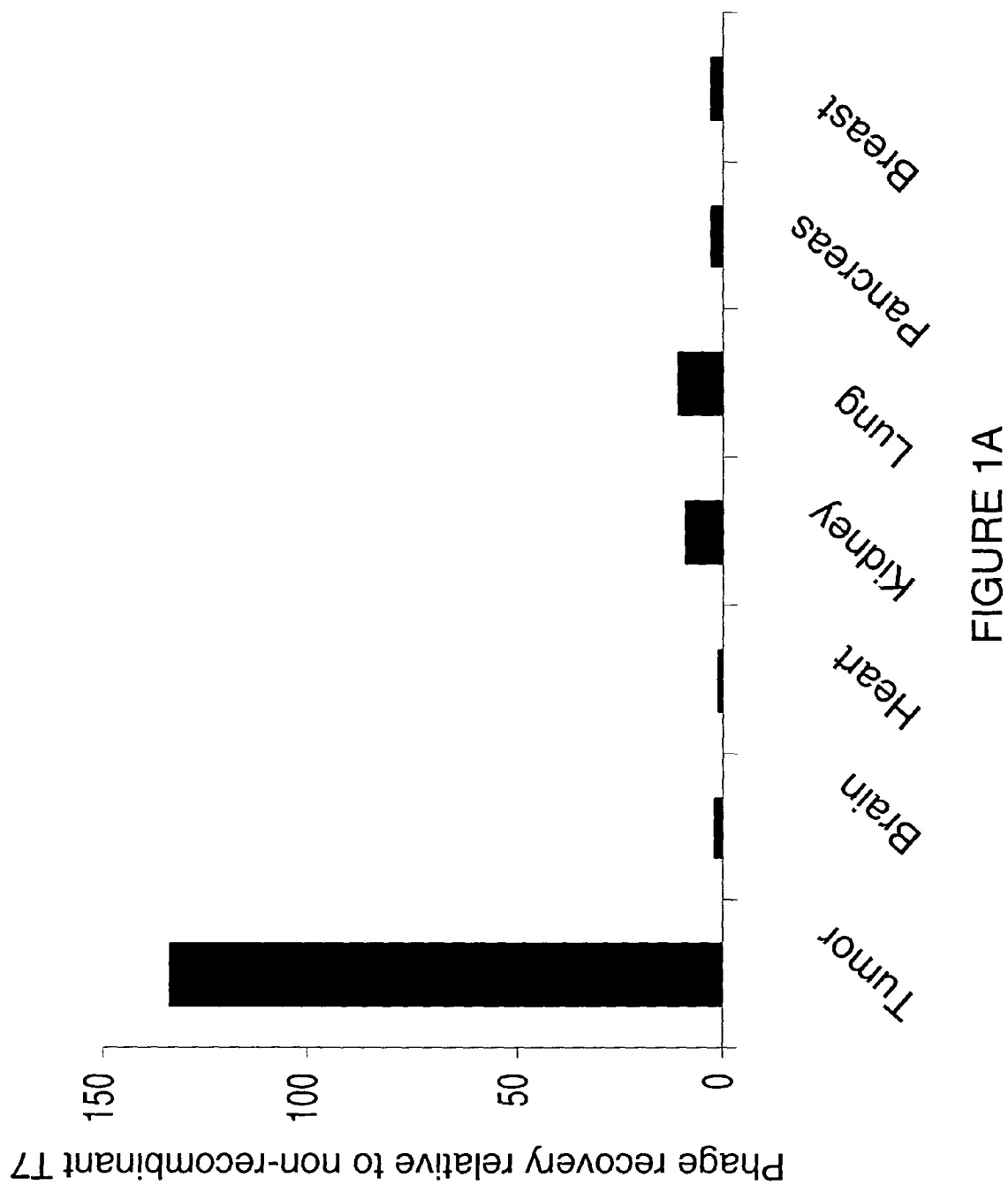

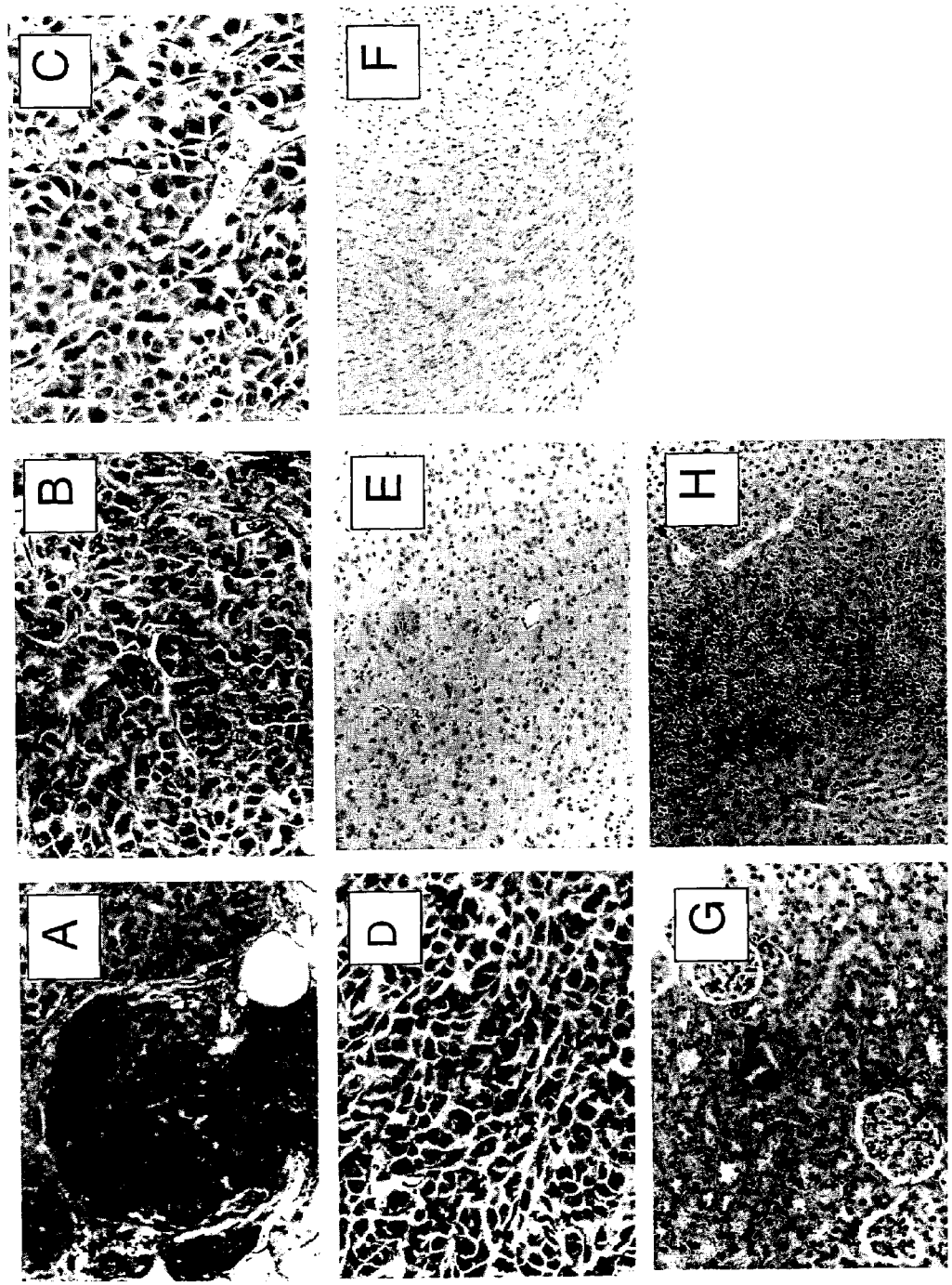

| | |
|---|---|
| Clone #3 | GERGEQGPPGPSVYSPHPSLAKGARGDPGFQGAHGEPGSRGEPGEPGTAGPPGPSVGDED |
| Coll-IV | GERGEQGPPGPSVYSPHPSLAKGARGDPGFQGAHGEPGSRGEPGEPGTAGPPGPSVGDED |
| | |
| Clone #3 | SMRGLPGEMGPKGFSGEPGSPARYLGPPGADGRPPGPQGVPGPAGPPGDGFLFGLKGSEG |
| Coll-IV | SMRGLPGEMGPKGFSGEPGSPARYLGPPGADGRPPGPQGVPGPAGPPGDGFLFGLKGSEG |
| | |
| Clone #3 | RVGYPGPSGFPGTRGQ - AW |
| Coll-IV | RVGYPGPSGFPGTRGQKGW |

FIGURE 4B

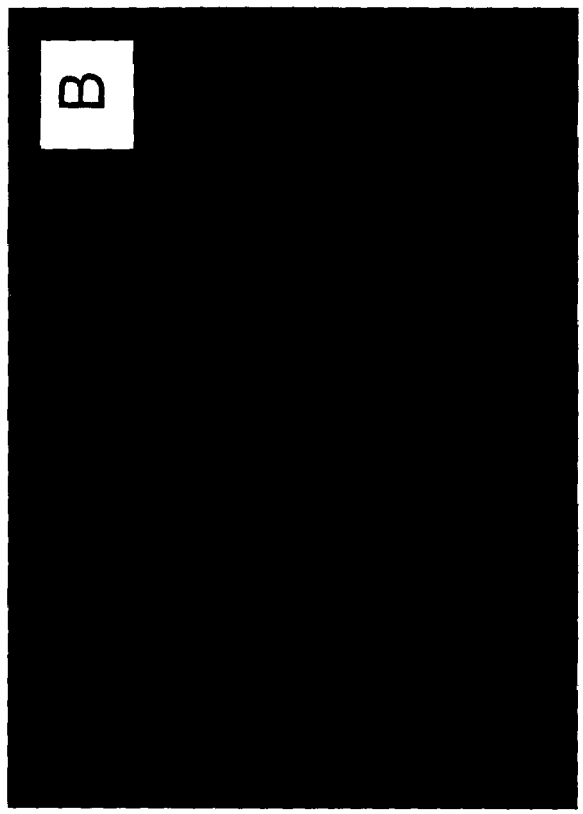
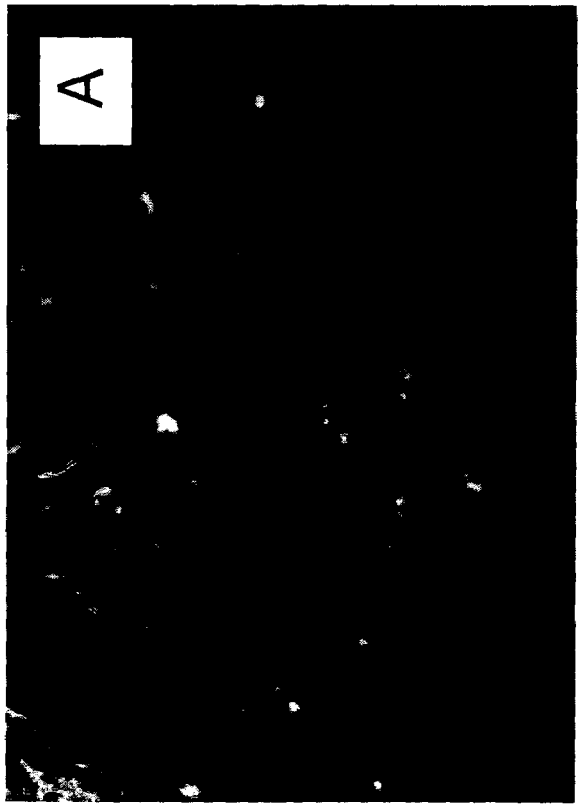
FIGURE 6

```
MGRDQRAVAG PALRRWLLLG TVTVGFLAQS VLAGVKKFDV PCGGRDCSGG CQCYPEKGGR
GQPGPVGPQG YNGPPGLQGF PGLQGRKGDK GERGAPGVTG PKGDVGARGV SGFPGADGIP
GHPGQGGPRG RPGYDGCNGT QGDSGPQGPP GSEGFTGPPG PQGPKGQKGE PYALPKEERD
RYRGEPGEPG LVGFQGPPGR PGHVGQMGPV GAPGRPGPPG PPGPKGQQGN RGLGFYGVKG
EKGDVGQPGP NGIPSDTLHP IIAPTGVTFH PDQYKGEKGS EGEPGIRGIS LKGEEGIMGF
PGLRGYPGLS GEKGSPGQKG SRGLDGYQGP DGPRGPKGEA GDPGPPGLPA YSPHPSLAKG
ARGDPGFPGA QGEPGSQGEP GDPGLPGPPG LSIGDGDQRR GLPGEMGPKG FIGDPGIPAL
YGGPPGPDGK RGPPGPPGLP GPPGPDGFLF GLKGAKGRAG FPGLPGSPGA PGPKGWKGDA
GECRCTEGDE AIKGLPGLPG PKGFAGINGE PGRKGDKGDP GQHGLPGFPG LKGVPGNIGA
PGPKGAKGDS RTITTKGERG QPGVPGVPGM KGDDGSPGRD GLDGFPGLPG PPGDGIKGPP
GDPGYPGIPG TKGTPGEMGP PGLGLPGLKG QRGFPGDAGL PGPPGFLGPP GPAGTPGQID
CDTDVKRAVG GDRQEAIQPG CIGGPKGLPG LPGPPGPTGA KGLRGIPGFA GADGGPGPRG
LPGDAGREGF PGPPGFIGPR GSKGAVGLPG PDGSPGPIGL PGPDGPPGER GLPGEVLGAQ
PGPRGDAGVP GQPGLKGLPG DRGPPGFRGS QGMPGMPGLK GQPGLPGPSG QPGLYGPPGL
HGFPGAPGQE GPLGLPGIPG REGLPGDRGD PGDTGAPGPV GMKGLSGDRG DAGFTGEQGH
PGSPGFKGID GMPGTPGLKG DRGSPGMDGF QGMPGLKGRP GFPGSKGEAG FFGIPGLKGL
AGEPGFKGSR GDPGPPGPPP VILPGMKDIK GEKGDEGPMG LKGYLGAKGI QGMPGIPGLS
GIPGLPGRPG HIKGVKGDIG VPGIPGLPGF PGVAGPPGIT GFPGFIGSRG DKGAPGRAGL
YGEIGATGDF GDIGDTINLP GRPGLKGERG TTGIPGLKGF FGEKGTEGDI GFPGITGVTG
VQGPPGLKGQ TGFPGLTGPP GSQGELGRIG LPGGKGDDGW PGAPGLPGFP GLRGIRGLHG
LPGTKGFPGS PGSDIHGDPG FPGPPGERGD PGEANTLPGP VGVPGQKGDQ GAPGERGPPG
SPGLQGFPGI TPPSNISGAP GDKGAPGIFG LKGYRGPPGP PGSAALPGSK GDTGNPGAPG
TPGTKGWAGD SGPQGRPGVF GLPGEKGPRG EQGFMGNTGP TGAVGDRGPK GPKGDPGFPG
APGTVGAPGI AGIPQKIAVQ PGTVGPQGRR GPPGAPGEMG PQGPPGEPGF RGAPGKAGPQ
GRGGVSAVPG FRGDEGPIGH QGPIGQEGAP GRPGSPGLPG MPGRSVSIGY LLVKHSQTDQ
EPMCPVGMNK LWSGYSLLYF EGQEKAHNQD LGLAGSCLAR FSTMPFLYCN PGDVCYYASR
NDKSYWLSTT APLPMMPVAE DEIKPYISRC SVCEAPAIAI AVHSQDVSIP HCPAGWRSLW
IGYSFLMHTA AGDEGGGQSL VSPGSCLEDF RATPFIECNG GRGTCHYYAN KYSFWLTTIP
EQSFQGSPSA DTLKAGLIRT HISRCQVCMK NL
```

COLLAGEN-BINDING MOLECULES THAT SELECTIVELY HOME TO TUMOR VASCULATURE AND METHODS OF USING SAME

This application claims benefit of the filing date of U.S. Provisional Application No. 60/509,048, filed Aug. 28, 2002, which was converted from U.S. Ser. No. 10/233,153, and which is incorporated herein by reference.

This invention was made with government support under CA74238, CA82713 and CA30199 awarded by the National Cancer Institute and grant HD31636 awarded by the National Institute of Child Health and Development. The government has certain rights in this invention.

BACKGROUND OF THE INVENTION

1. Field of the Invention

The present invention relates generally to the fields of molecular medicine and cancer biology and, more specifically, to collagen-binding molecules that selectively home to tumor vasculature.

2. Background Information

A major hurdle to advances in treating cancer is the relative lack of agents that can selectively target the cancer while sparing normal tissue. For example, radiation therapy and surgery, which generally are localized treatments, can cause substantial damage to normal tissue in the treatment field, resulting in scarring and loss of normal tissue. Chemotherapy, in comparison, which generally is administered systemically, can cause substantial damage to organs such as the bone marrow, mucosae, skin and small intestine, which undergo rapid cell turnover and continuous cell division. As a result, undesirable side effects such as nausea, loss of hair and drop in blood cell count often occur when a cancer patient is treated intravenously with a chemotherapeutic drug. Such undesirable side effects can limit the amount of a drug that can be safely administered, thereby hampering survival rate and impacting the quality of patient life.

Thus, there is a need for new therapeutic strategies for selectively targeting tumors and reducing the side effects associated with systemic therapy. The present invention satisfies this need by providing molecules that selectively home to tumor vasculature and which are suitable for selectively targeting chemotherapeutic drugs, gene therapy vectors or other agents to the tumor vasculature. Related advantages also are provided.

SUMMARY OF THE INVENTION

The present invention provides an isolated peptide or peptidomimetic which has a length of less than 100 residues and includes the amino acid sequence CREKA (SEQ ID NO: 1) or a peptidomimetic thereof. Such an isolated peptide or peptidomimetic can have, for example, a length of less than 50 residues or a length of less than 20 residues. In particular embodiments, the invention provides a peptide that includes the amino acid sequence CREKA (SEQ ID NO: 1) and has a length of less than 20, 50 or 100 residues.

The present invention further provides a conjugate containing a therapeutic agent linked to a homing molecule that selectively homes to tumor vasculature and selectively binds collagen. In one embodiment, the invention provides a conjugate containing a homing molecule that selectively homes to tumor vasculature and that selectively binds non-helical collagen. In another embodiment, the invention provides a conjugate containing a homing molecule that selectively homes to breast tumor vasculature and that selectively binds collagen. In another embodiment, the invention provides a conjugate containing a homing molecule that selectively homes to tumor vasculature and that selectively binds collagen IV. In yet another embodiment, the invention provides a conjugate containing a homing molecule that selectively homes to tumor vasculature and that selectively binds denatured collagen IV in preference to native collagen IV. In a further embodiment, the invention provides a conjugate containing a homing molecule that selectively homes to tumor vasculature and that selectively binds the alpha 2 chain of collagen IV. In yet a further embodiment, the invention provides a conjugate containing a homing molecule that selectively homes to tumor vasculature and selectively binds collagen and which is not an antibody or antigen-binding fragment thereof.

A variety of homing molecules that selectively home to tumor vasculature are useful in the conjugates of the invention. Such homing molecules include, without limitation, homing peptides and peptidomimetics. In one embodiment, the homing peptide or peptidomimetic portion of the conjugate has a length of at most 200 residues. In another embodiment, the homing peptide or peptidomimetic portion of the conjugate has a length of at most 50 residues. In a further embodiment, a conjugate of the invention contains a homing peptide or peptidomimetic that includes the amino acid sequence CREKA (SEQ ID NO: 1) or a conservative variant or peptidomimetic thereof. In another embodiment, a conjugate of the invention contains a homing peptide or peptidomimetic that includes the amino acid sequence CREKA (SEQ ID NO: 1) or a peptidomimetic thereof. In still a further embodiment, a conjugate of the invention contains a homing peptide that includes the amino acid sequence CREKA (SEQ ID NO: 1).

A variety of therapeutic agents are useful in the conjugates of the invention including, without limitation,-cancer chemotherapeutic agents, cytotoxic agents, anti-angiogenic agents, polypeptides, nucleic acid molecules and small molecules. As non-limiting examples, the invention provides a conjugate containing a therapeutic agent linked to a homing molecule that selectively homes to tumor vasculature and selectively binds collagen, where the therapeutic agent is a cancer chemotherapeutic agent, cytotoxic agent, anti-angiogenic agent, polypeptide, nucleic acid molecule or small molecule. As further non-limiting examples, the invention provides a conjugate containing a therapeutic agent linked to a homing peptide or peptidomimetic that selectively homes to tumor vasculature and selectively binds collagen, where the therapeutic agent is a cancer chemotherapeutic agent, cytotoxic agent, anti-angiogenic agent, polypeptide, nucleic acid molecule or small molecule. As additional non-limiting examples, the invention provides a conjugate that contains a therapeutic agent linked to a homing peptide or peptidomimetic containing the amino acid sequence CREKA (SEQ ID NO: 1), or a conservative variant or peptidomimetic thereof, that selectively homes to tumor vasculature and selectively binds collagen, where the therapeutic agent is a cancer chemotherapeutic agent, cytotoxic agent, anti-angiogenic agent, polypeptide, nucleic acid molecule or small molecule. Also provided herein is a conjugate that contains a therapeutic agent linked to a homing peptide or peptidomimetic containing the amino acid sequence CREKA (SEQ ID NO: 1), or a peptidomimetic thereof, that selectively homes to tumor vasculature and that selectively binds collagen, where the therapeutic agent is a cancer chemotherapeutic agent, cytotoxic agent, anti-angiogenic agent, polypeptide, nucleic acid molecule or small molecule. Further provided herein is a conjugate containing a therapeutic agent linked to a homing peptide containing the amino acid sequence CREKA (SEQ ID NO: 1) that selectively homes to tumor vasculature and selectively binds collagen, where the therapeutic agent is a cancer chemotherapeutic agent, cytotoxic agent, anti-angiogenic agent, polypeptide, nucleic acid molecule or small molecule. Any of these or other conjugates of the invention can optionally include a virus moiety such as a phage.

The present invention also provides a conjugate containing a therapeutic agent and at least two homing molecules that each selectively homes to tumor vasculature and selectively binds collagen. The two homing molecules can each independently contain, for example, the amino acid sequence CREKA (SEQ ID NO: 1) or a conservative variant or peptidomimetic thereof. Further provided by the invention is a conjugate containing a therapeutic agent and at least ten homing molecules that each selectively homes to tumor vasculature and selectively binds collagen. The ten homing molecules can each independently contain, for example, the amino acid sequence CREKA (SEQ ID NO: 1) or a conservative variant or peptidomimetic thereof. The invention also provides a conjugate containing a therapeutic agent and at least 100 homing molecules that each selectively homes to tumor vasculature and selectively binds collagen. The 100 homing molecules included in the conjugate can each independently contain, for example, the amino acid sequence CREKA (SEQ ID NO: 1) or a conservative variant or peptidomimetic thereof. Any of the above conjugates of the invention containing multiple homing molecules can optionally include a virus moiety such as a phage.

The present invention further provides a method of directing a moiety to tumor vasculature in a subject by administering to the subject a conjugate which contains the moiety linked to a homing molecule that selectively homes to tumor vasculature and selectively binds collagen, thereby directing the moiety to tumor vasculature. In one embodiment, the homing molecule selectively homes to tumor vasculature and selectively binds non-helical collagen. In another embodiment, a method of the invention is practiced with a homing molecule that selectively homes to breast tumor vasculature and selectively binds collagen. In yet another embodiment, a method of the invention is practiced with a homing molecule that selectively homes to tumor vasculature and selectively binds collagen IV. In a further embodiment, a method of the invention is practiced with a homing molecule that selectively homes to tumor vasculature and selectively binds denatured collagen IV in preference to native collagen IV. In another embodiment, a method of the invention is practiced with a homing molecule that selectively homes to tumor vasculature and selectively binds the alpha 2 chain of collagen IV. In yet a further embodiment, a method of the invention is practiced with a homing molecule that selectively homes to tumor vasculature and selectively binds collagen and which is not an antibody or antigen-binding fragment thereof.

A variety of homing molecules can be useful in the methods of the invention for directing a moiety to tumor vasculature. Useful homing molecules include, yet are not limited to, homing peptides or peptidomimetics such as those including the amino acid seguence CREKA (SEQ ID NO: 1) or a conservative variant or peptidomimetic thereof. In one embodiment, a method of the invention for directing a moiety to tumor vasculature is practiced with a homing molecule that includes the amino acid sequence CREKA (SEQ ID NO: 1), or a peptidomimetic thereof. In a further embodiment, a method of the invention for directing a moiety to tumor vasculature is practiced with a homing molecule that includes the amino acid sequence CREKA (SEQ ID NO: 1). A variety of moieties can be targeted to tumor vasculature according to a method of the invention including, without limitation, therapeutic agents, detectable agents and phage. As non-limiting examples, therapeutic agents to be directed to tumor vasculature include cancer chemotherapeutic agents, cytotoxic agents, anti-angiogenic agents, polypeptides, nucleic acid molecules and small molecules.

Also provided herein is a method of imaging tumor vasculature in a subject by (a) administering to the subject a conjugate containing a detectable agent linked to a homing molecule that selectively homes to tumor vasculature and selectively binds collagen; and (b) detecting the conjugate, thereby imaging tumor vasculature. In one embodiment, a method of the invention is practiced with a homing molecule that selectively homes to tumor vasculature and selectively binds to non-helical collagen. In another embodiment, an imaging method of the invention is practiced with a homing molecule that selectively homes to tumor vasculature and selectively binds collagen and which is not an antibody or antigen-binding fragment thereof. In a further embodiment, a method of the invention is used to image breast tumor vasculature.

A variety of homing molecules can be useful in the imaging methods of the invention, including homing peptides and peptidomimetics such as homing peptides or peptidomimetics containing the amino acid sequence CREKA (SEQ ID NO: 1) or a conservative variant or peptidomimetic thereof. In one embodiment, the invention provides an imaging method that relies on a homing peptide or peptidomimetic containing the amino acid sequence CREKA (SEQ ID NO: 1) or a peptidomimetic thereof. In another embodiment, the invention provides an imaging method that relies on a homing peptide containing the amino acid sequence CREKA (SEQ ID NO: 1). Detectable agents useful in the imaging methods of the invention encompass, yet are not limited to, fluorophores such as fluorescein and rhodamine and radionuclides such as indium-111, technetium-99, carbon-11 and carbon-13.

The present invention additionally provides a method of reducing the number of tumor vessels in a subject by administering to the subject a conjugate which includes a therapeutic agent linked to a homing molecule that selectively homes to tumor vasculature and selectively binds collagen, thereby reducing the number of tumor vessels in the subject. A method of the invention can be useful, for example, for reducing the number of breast tumor vessels. In one embodiment, a method of the invention for reducing the number of tumor vessels is practiced with a homing molecule that selectively homes to tumor vasculature and selectively binds non-helical collagen. In another embodiment, a method of the invention for reducing the number of tumor vessels is practiced with a homing molecule that selectively homes to tumor vasculature and selectively binds collagen and which is not an antibody or antigen-binding fragment thereof. Homing molecules useful in the invention encompass, without limitation, homing peptides and peptidomimetics such as those including the amino acid sequence CREKA (SEQ ID NO: 1) or a conservative variant or peptidomimetic thereof. A method of the invention can be practiced, for example, with a homing peptide or peptidomimetic containing the amino acid sequence CREKA (SEQ ID NO: 1) or a peptidomimetic thereof. A method of the invention also can be practiced, for example, with a homing peptide containing the amino acid sequence CREKA (SEQ ID NO: 1). In a method of the invention for reducing the number of tumor vessels, a variety of therapeutic agents can be incorporated into the conjugate administered to the subject, including, for example, cancer chemotherapeutic agents, cytotoxic agents, and anti-angiogenic agents.

Also provided herein is a method of treating cancer in a subject by administering to the subject a conjugate which contains a therapeutic agent linked to a homing molecule that selectively homes to tumor vasculature and selectively binds collagen. As a non-limiting example, a method of the invention for treating cancer can be useful for treating breast cancer. Homing molecules useful in the invention include those which selectively home to tumor vasculature and selectively bind non-helical collagen. Homing molecules useful in the invention also include those which selectively home to tumor vasculature and selectively bind collagen IV, and those which selectively home to tumor vasculature and selectively bind denatured collagen IV in preference to native collagen IV. Homing molecules useful in the invention further include those which selectively home to tumor vasculature and selectively bind the alpha 2 chain of collagen IV. In one embodiment, a method of the invention for treating cancer relies on a homing molecule that selectively homes to tumor vasculature and selectively binds collagen and which is not an antibody or antigen-binding fragment thereof.

A variety of homing molecules can be included in a conjugate useful for treating cancer according to a method of the invention. In one embodiment, a method of the invention is practiced with a conjugate that contains a homing peptide or peptidomimetic. In another embodiment, a method of the invention is practiced with a conjugate in which the peptide or peptidomimetic portion of the conjugate has a length of at most 200 residues. In another embodiment, a method of the invention is practiced with a conjugate in which the peptide or peptidomimetic portion of the conjugate has a length of at most 50 residues. In yet another embodiment, a method of the invention is practiced with a conjugate which contains a homing peptide or peptidomimetic that includes the amino acid sequence CREKA (SEQ ID NO: 1) or a conservative variant or peptidomimetic thereof. In still another embodiment, a method of the invention is practiced with a conjugate containing a homing peptide or peptidomimetic that includes the amino acid sequence CREKA (SEQ ID NO: 1), or a peptidomimetic thereof. In a further embodiment, a method of the invention is practiced with a conjugate containing a homing peptide which includes the amino acid sequence CREKA (SEQ ID NO: 1). A conjugate useful for treating cancer according to a method of the invention incorporates a therapeutic agent such as, without limitation, a cancer chemotherapeutic agent, cytotoxic agent, anti-angiogenic agent, polypeptide, nucleic acid molecule or small molecule and can optionally further include one or more additional components such as a phage or other viral moiety.

BRIEF DESCRIPTION OF THE DRAWINGS

FIG. 2 shows localization of CREKA (SEQ ID NO: 1)-displaying phage in mouse breast tumors. Phage were detected 15 minutes after injection by staining with anti-T7 phage antibodies. (A) CREKA (SEQ ID NO: 1)-phage staining in MMTV PyMT mammary carcinomas; (B) CREKA (SEQ ID NO: 1)-phage staining in MDA-MB-435 xenograft tumors; (C) Non-recombinant T7 phage staining in breast tumor tissue; (D) Staining of breast tumor tissue with control antibody; (E) CREKA (SEQ ID NO: 1)-phage staining in brain; (F) CREKA (SEQ ID NO: 1)-phage staining in heart; (G) CREKA (SEQ ID NO: 1)-phage staining in kidney; (H) CREKA (SEQ ID NO: 1)-phage staining in liver.

FIG. 6 shows the distribution of FITC-CREKA (SEQ ID NO: 1) and collagen IV in tumor tissue. (A) Collagen IV staining of a tumor from a MMTV PyMT mouse injected with FITC-CREKA (SEQ ID NO: 1). (B) Collagen IV staining of a tumor from a mouse not injected with FITC-CREKA (SEQ ID NO: 1).

FIG. 7 shows the amino acid sequence of the human collagen IV α2 chain (SEQ ID NO: 4). See, also, Genbank NM_001846.

DETAILED DESCRIPTION OF THE INVENTION

Figure 1B:
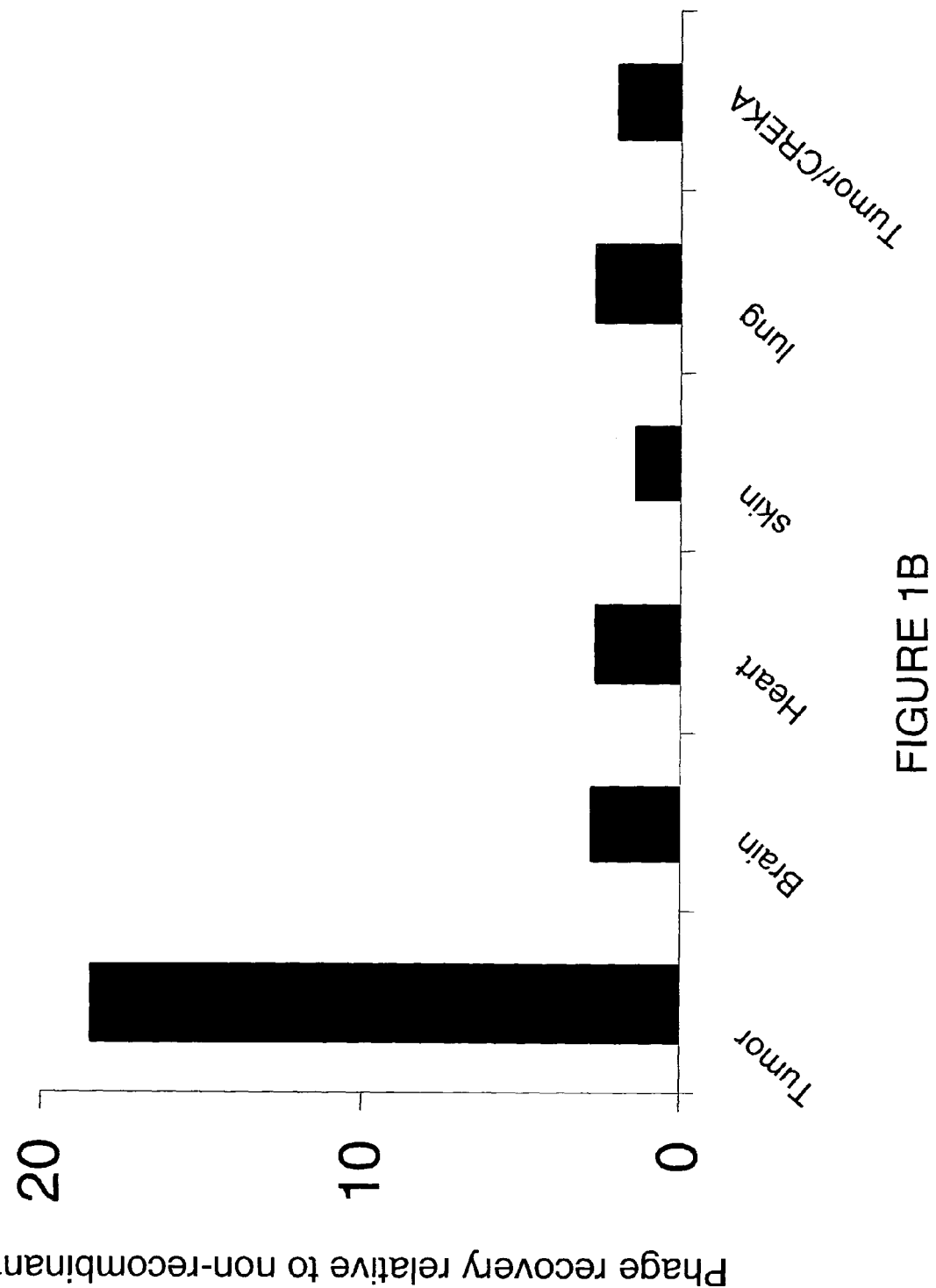
FIG. 1 shows the specificity of CREKA (SEQ ID NO: 1) phage homing to breast tumors. (A) MMTV PyMT mice. (B) Mice bearing MDA-MB-435 xenografts. Phage preparations were injected into tumor-bearing mice and recovered from breast tumor or the indicated normal tissue. One of several representative experiments is shown, with the number of pfu recovered represented by black bars. "Tumor/CREKA" indicates phage recovery from breast tumors subsequent to co-injection of free CREKA (SEQ ID NO: 1) peptide. "Tumor/control peptide" indicates phage recovery from breast tumors subsequent to co-injection of free control peptide.

The present invention is directed, in part, to the discovery of homing molecules which selectively home to tumor vasculature, for example, selectively home to the matrix of breast tumor vasculature. As disclosed herein, peptide CREKA (SEQ ID NO: 1) was identified by in vivo panning as selectively homing to breast tumor vasculature as compared to the vasculature of a variety of normal organs. As shown in FIG. 1A, about 130 times more of the CREKA (SEQ ID NO: 1)-displaying phage than control T7 phage homed to breast tumor vasculature in MMTV PyMT mice; furthermore, the CREKA (SEQ ID NO: 1)-displaying phage did not home to most other non-tumor tissues, including normal brain, heart, kidney, lung, pancreas and breast tissue. The CREKA (SEQ ID NO: 1)-displaying phage also homed to the vasculature of MDA-MB-435 human breast cancer xenografts with a 20-fold specificity over non-recombinant phage (see FIG. 1B). As further disclosed herein, tumor homing of the CREKA (SEQ ID NO: 1) phage was specific, since coinjection of free peptide SEQ ID NO: 1 inhibited phage recovery from breast tumor tissue (Example 1 and FIG. 1B).

As further disclosed herein in Example 2, immunoperoxidase staining showed that CREKA (SEQ ID NO: 1)-displaying phage were present in MMTV PyMT tumors (FIG. 2A) and MDA-MB-435 xenografts (FIG. 2B) fifteen minutes after intravenous injection of the phage while similarly injected non-recombinant T7 phage were undetectable in the tumors (FIG. 2C). No CREKA (SEQ ID NO: 1)-displaying phage were detected in control normal organs such as the brain, kidney and heart (FIGS. 2E, 2F and 2G, respectively). Although normal liver stained positive for the CREKA (SEQ ID NO: 1)-phage (FIG. 2H), control T7 phage also localized to normal liver, indicating non-specific uptake by the reticuloendothelial system.

Figure 3:
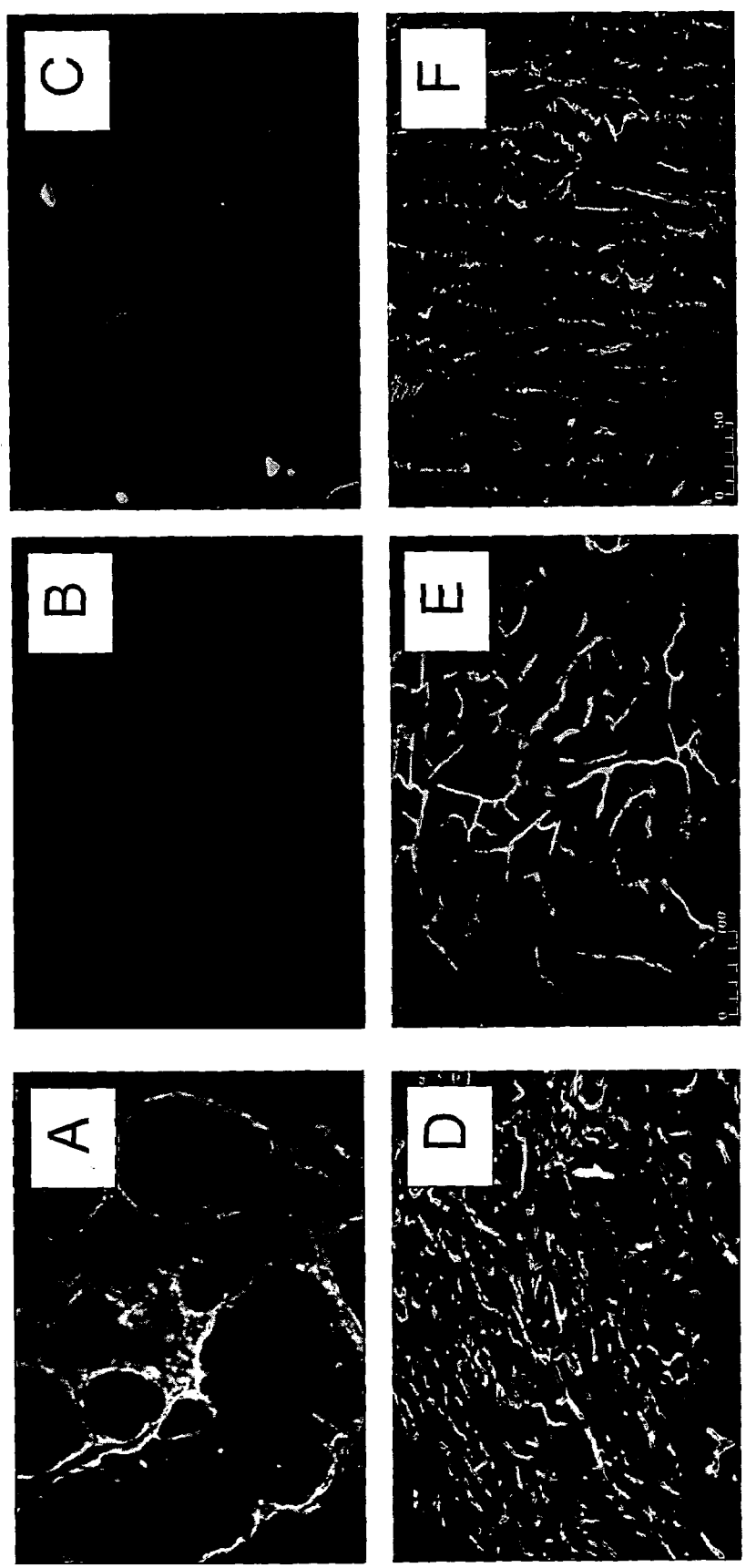
FIG. 3 shows localization of fluorescein-labeled and rhodamine-labeled CREKA (SEQ ID NO: 1) peptide in MMTV PyMT tumors. (A) FITC-CREKA (SEQ ID NO: 1) fluorescence in MMTV PyMT tumors 15 minutes after injection. (B) FITC-CREKA (SEQ ID NO: 1) fluorescence in brain 15 minutes after injection. (C) FITC-CREKA (SEQ ID NO: 1) fluorescence in liver 15 minutes after injection. (D) FITC-CREKA (SEQ ID NO: 1) fluorescence in MMTV PyMT tumors two hours following injection. Nuclei were counter-stained with DAPI, and tumor vasculature was visualized by intravenous injection of FITC-tomato lectin. (E) Tumor vasculature of MMTV PyMT tumors visualized by intravenous injection of FITC-tomato-lectin (F) Rhodamine-CREKA (SEQ ID NO: 1) and FITC-tomato-lectin staining in MMTV PyMT mouse heart tissue counter-stained with DAPI.

The results shown in FIG. 3 demonstrate that fluorescein (FITC) and rhodamine-labeled CREKA (SEQ ID NO: 1) peptides also localized to MMTV PyMT tumors fifteen minutes after intravenous injection but were not present in normal tissues such as the brain or liver (compare FIG. 3A with FIGS. 3B and 3C). The peptides were found primarily in the tumor periphery fifteen minutes after injection but could be detected in the entire tumor after two hours, localizing outside the blood vessels as shown in FIG. 3D. The localization of CREKA (SEQ ID NO: 1) peptide to breast tumor vessels was confirmed by injection of rhodamine-labeled CREKA (SEQ ID NO: 1) peptide with FITC-tomato-lectin, which stains blood vessels, in MMTV PyMT mice (see FIG. 3E). These results demonstrate that CREKA (SEQ ID NO: 1)-displaying phage and labeled CREKA (SEQ ID NO: 1) peptides quickly localize to the vasculature of human or murine breast tumors in preference to the vasculature of normal organs.

Figure 4A:
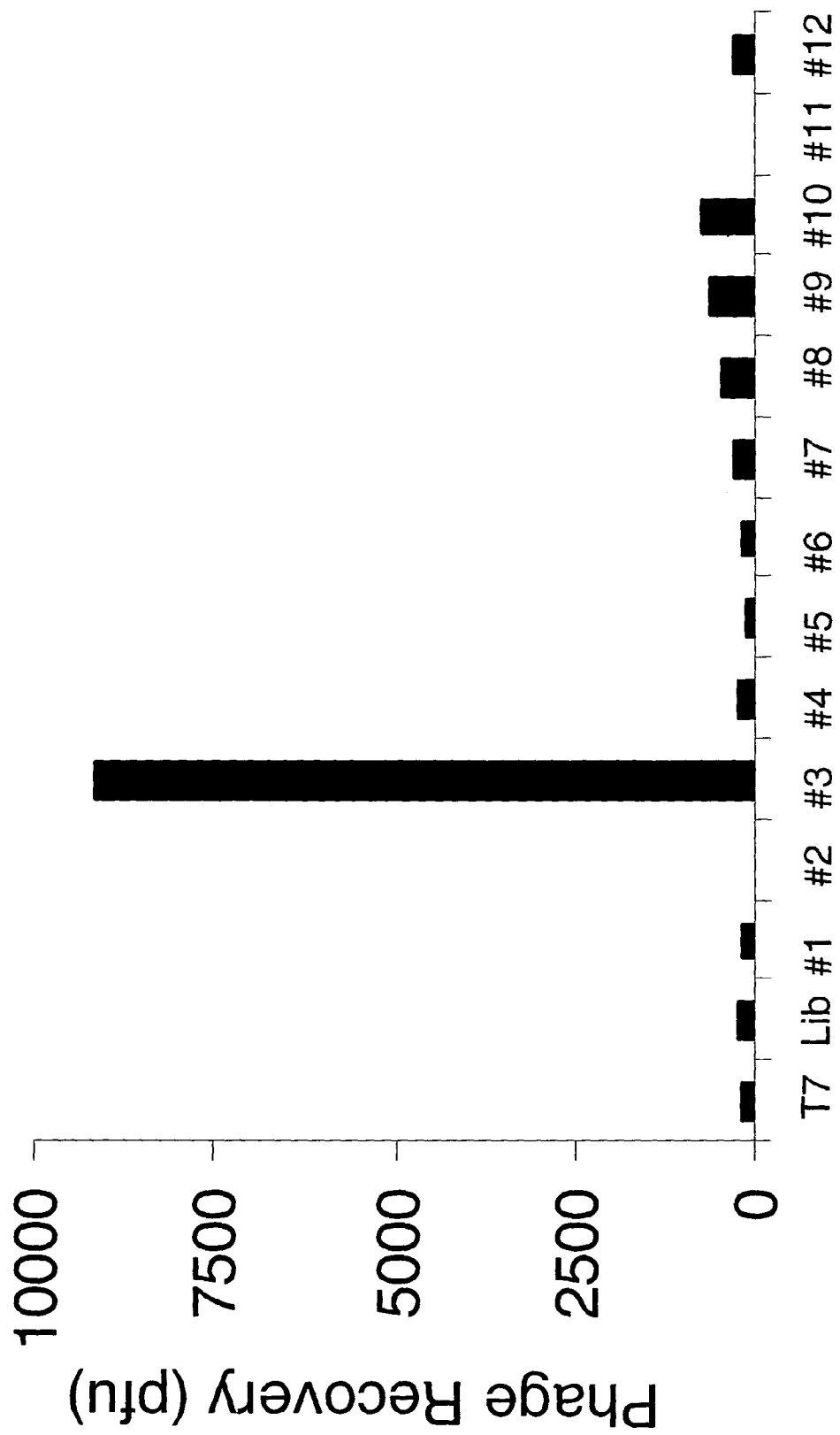
FIG. 4 shows the results obtained by screening for binding on immobilized CREKA (SEQ ID NO: 1) peptide. (A) Phage recovery of twelve individual clones on immobilized CREKA (SEQ ID NO: 1) plates. (B) Amino acid sequence of the CREKA (SEQ ID NO: 1)-binding phage displayed protein fragment Clone #3. The cDNA encodes a 138 amino acid fragment (SEQ ID NO: 2) related to the corresponding portion of the collagen IV alpha-2 chain (SEQ ID NO: 3).

The present invention further is directed to the surprising discovery that a collagen such as collagen IV can serve as a receptor for the CREKA (SEQ ID NO: 1) peptide in the matrix of tumor vasculature. As disclosed herein in Example 3, a murine breast cancer cDNA library was screened against immobilized CREKA (SEQ ID NO: 1) peptide. One clone (#3) bound avidly to the CREKA (SEQ ID NO: 1)-coated surface but not to an uncoated surface treated with the blocking buffer only (see FIG. 4A). As shown in FIG. 4B, this clone encodes a 138 amino acid fragment related to a portion of the collagen IV alpha-2 chain containing Gly-X-Y repeats, characteristic of the triple helical portion of collagen IV.

Figure 5A:
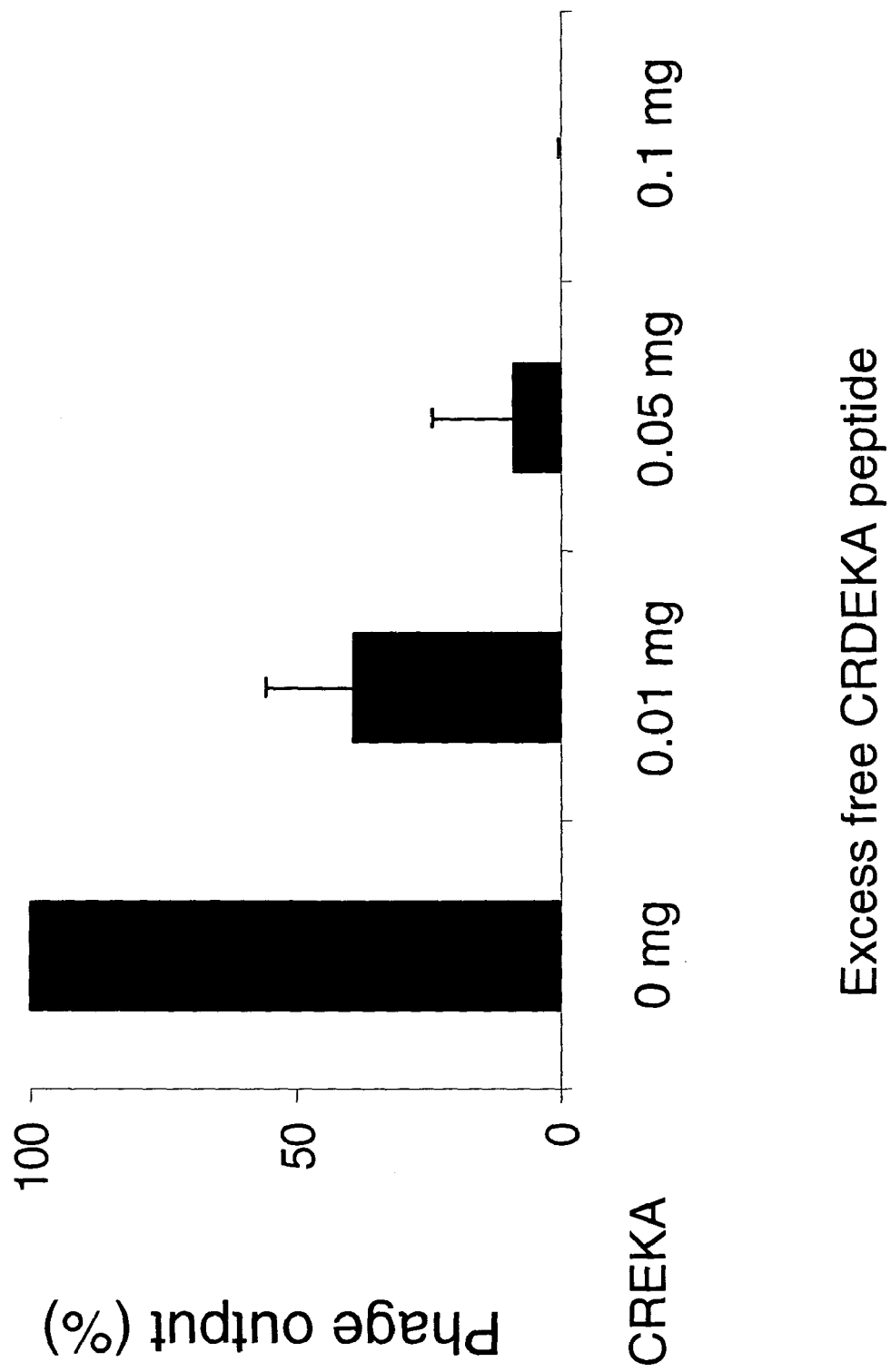
FIG. 5 shows specificity of CREKA (SEQ ID NO: 1) binding to collagen. (A) Inhibition of phage displaying the clone #3 collagen IV fragment (SEQ ID NO: 2) binding to immobilized CREKA (SEQ ID NO: 1) by soluble CREKA (SEQ ID NO: 1) peptide. The data shown are representative of three separate experiments. (B) Binding of phage displaying clone #3 (SEQ ID NO: 2) to immobilized CREKA (SEQ ID NO: 1) in the presence of fibronectin (100 µg/ml), anti-collagen IV antibody, or control antibody. (C) Phage displaying CREKA (SEQ ID NO: 1) binding to immobilized collagen I, II, IV and X in native and denatured states.
Figure 5B:
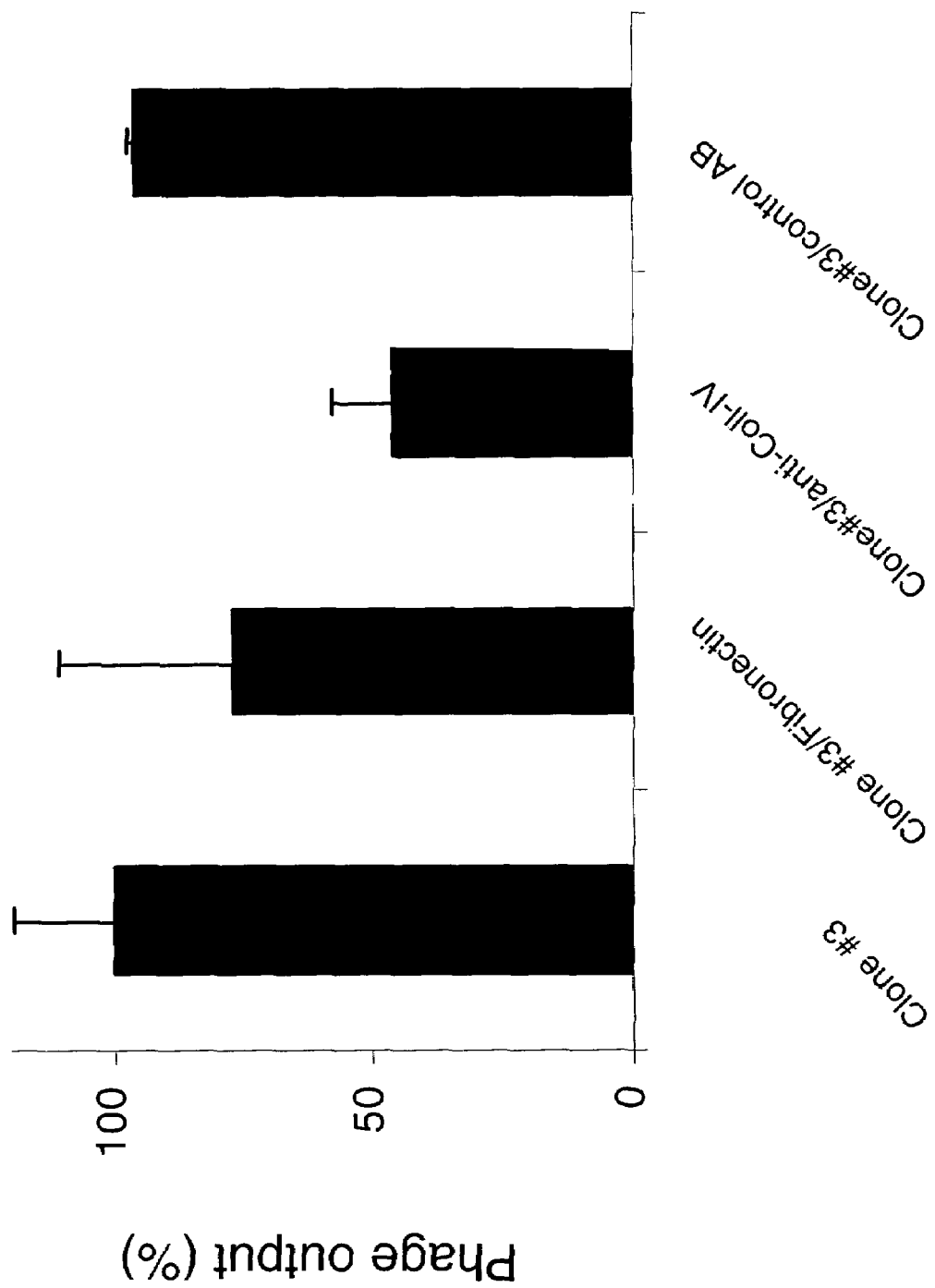

As further demonstrated in FIG. 5A, the observed interaction between CREKA (SEQ ID NO: 1) and the collagen IV fragment of clone #3 (SEQ ID NO: 2) is specific, as it could be inhibited by an excess of cognate CREKA (SEQ ID NO: 1) peptide in a dose-dependent manner. Furthermore, as shown in FIG. 5B, rabbit anti-mouse collagen IV serum, but not control serum, blocked the interaction between the phage-displayed collagen fragment and immobilized CREKA (SEQ ID NO: 1). In contrast, fibronectin, which binds to various collagens in their non-triple helical form, did not significantly reduce binding of CREKA (SEQ ID NO: 1)-displaying phage (FIG. 5B), indicating that the collagen binding site for CREKA (SEQ ID NO: 1) is distinct from that of fibronectin.

Figure 5C:
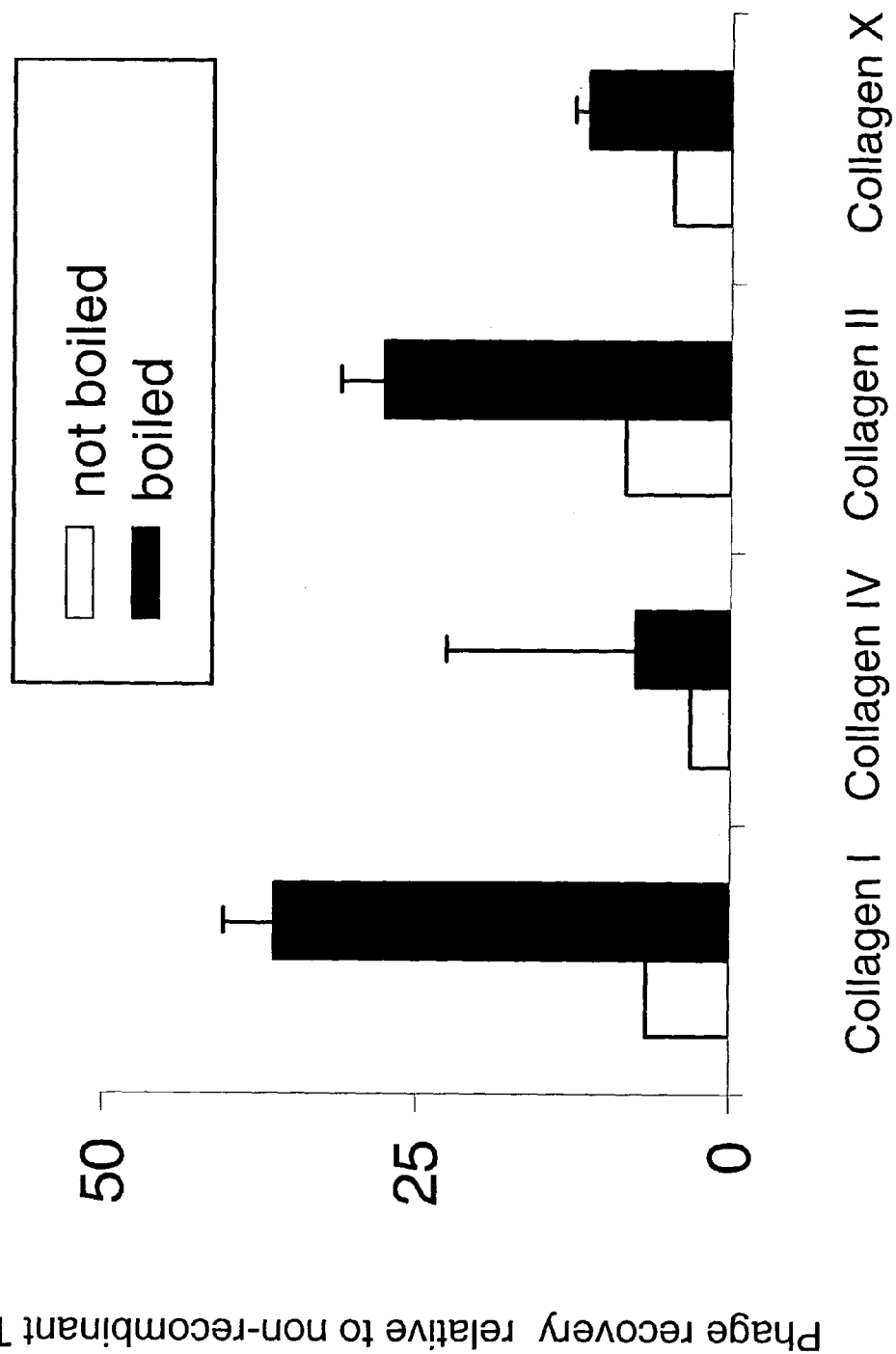

As further disclosed herein in Example 3, CREKA (SEQ ID NO: 1)-displaying phage also were assayed for the ability to bind surfaces coated with several different collagens. FIG. 5C shows that CREKA (SEQ ID NO: 1) phage bound to each of the collagens tested: collagens I, II, IV and X. Furthermore, denaturation of the collagens by boiling enhanced the CREKA (SEQ ID NO: 1)-phage binding, indicating that non-helical collagen can be a receptor for CREKA (SEQ ID NO: 1) and other tumor homing molecules in tumor vasculature. These results were corroborated by the ability of gelatin, which is denatured collagen I, to completely block in vivo binding of CREKA (SEQ ID NO: 1) to collagen. The CREKA (SEQ ID NO: 1) peptide shares with fibronectin the ability to preferentially bind denatured collagen (Engvall et al., Cell 29:475-482 (1982)); however, as described above, fibronectin does not compete for CREKA (SEQ ID NO: 1) binding to collagen, indicating that CREKA (SEQ ID NO: 1) and fibronectin bind to different regions of denatured collagen.

As additionally disclosed herein, localization of collagen IV was compared to the localization of CREKA (SEQ ID NO: 1) peptide in breast tumors. As shown in FIG. 6, FITC-CREKA (SEQ ID NO: 1) partially co-localized with collagen IV in MMTV-PyMT tumors while a FITC-labeled control peptide did not, further supporting a role for collagen IV as a receptor for the CREKA (SEQ ID NO: 1) peptide in tumor vasculature. In sum, these results demonstrate that the CREKA (SEQ ID NO: 1) peptide binds a collagen IV α-2 chain related protein and further indicate that collagen IV or a related collagen can act as a receptor for tumor homing molecules in tumor vasculature.

Based on these findings, the present invention provides homing molecules and conjugates useful, for example, for directing a moiety to tumor vasculature, for reducing the number of tumor vessels in a subject and for treating cancer. The conjugates of the invention also can be useful, for example, for imaging tumor vasculature such as breast tumor vasculature.

Thus, the present invention provides an isolated peptide or peptidomimetic which has a length of less than 100 residues and which includes the amino acid sequence CREKA (SEQ ID NO: 1) or a peptidomimetic thereof. Such an isolated peptide or peptidomimetic can have, for example, a length of less than 50 residues or a length of less than 20 residues. In particular embodiments, the invention provides a peptide that includes the amino acid sequence CREKA (SEQ ID NO: 1) and has a length of less than 20, 50 or 100 residues.

The peptides and peptidomimetics of the invention are provided in isolated form. As used herein in reference to a peptide or peptidomimetic of the invention, the term "isolated" means a peptide or peptidomimetic that is in a form that is relatively free from material such as contaminating polypeptides, lipids, nucleic acids and other cellular material that normally is associated with the peptide or peptidomimetic in a cell or that is associated with the peptide or peptidomimetic in a library or in a crude preparation.

The peptides and peptidomimetics of the invention, including the bifunctional, multivalent and homing peptides and peptidomimetics discussed below, can have a variety of lengths. A peptide or peptidomimetic of the invention can have, for example, a relatively short length of less than six, seven, eight, nine, ten, 12, 15, 20, 25, 30, 35 or 40 residues. A peptide or peptidomimetic of the invention also can be useful in the context of a significantly longer sequence. For example, as disclosed herein, the CREKA peptide (SEQ ID NO: 1) maintained the ability to home when fused to a phage coat protein, confirming that a peptide of the invention can have selective homing activity when embedded in a larger protein sequence. Thus, a peptide or peptidomimetic of the invention can have, for example, a length of up to 50, 100, 150, 200, 250, 300, 400, 500, 1000 or 2000 residues. In particular embodiments, a peptide or peptidomimetic of the invention has a length of at least 10, 20, 30, 40, 50, 60, 70, 80, 90, 100 or 200 residues. In further embodiments, a peptide or peptidomimetic of the invention has a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

The present invention also provides an isolated peptide or peptidomimetic containing the amino acid sequence CREKA (SEQ ID NO: 1), or a conservative variant or peptidomimetic of one of this sequence. As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. As non-limiting examples, conservative variants of CREKA (SEQ ID NO: 1) include SREKA (SEQ ID NO: 5); CKEKA (SEQ ID NO: 6); CRDKA (SEQ ID NO: 7); CRERA (SEQ ID NO: 8); CREKV (SEQ ID NO: 9); SKEKA (SEQ ID NO: 10); SRDKA (SEQ ID NO: 11); SRERA (SEQ ID NO: 12); SREKV (SEQ ID NO: 13); CKDKA (SEQ ID NO: 14); CKERA (SEQ ID NO: 15); CKEKV (SEQ ID NO: 16); CRDRA (SEQ ID NO: 17); CRDKV (SEQ ID NO: 18); and CRERV (SEQ ID NO: 19). It is understood that conservative variants of CREKA (SEQ ID NO: 1) encompass sequences containing one, two, three, four or more amino acid substitutions relative to SEQ ID NO: 1 and that such variants can include naturally and non-naturally occurring amino acid analogs.

The invention further provides a chimeric protein containing a peptide or peptidomimetic of the invention, or a homing peptide or peptidomimetic of the invention, fused to a heterologous protein. The invention provides, for example, a chimeric protein containing a homing peptide or peptidomimetic that selectively homes to tumor vasculature and selectively binds collagen such as non-helical collagen or collagen IV. In one embodiment, the heterologous protein has a therapeutic activity such as cytokine activity, cytotoxic activity or pro-apoptotic activity. In a further embodiment, the heterologous protein is an antibody or antigen-binding fragment thereof. In other embodiments, the chimeric protein includees a peptide or peptidomimetic containing the amino acid sequence CREKA (SEQ ID NO: 1), or a conservative variant or peptidomimetic thereof, fused to a heterologous protein. The term "heterologous," as used herein in reference to a protein fused to a peptide or peptidomimetic of the invention, means a protein derived from a source other than the gene encoding the peptide of the invention or from which the peptidomimetic is derived. A chimeric protein of the invention can have a variety of lengths including, but not limited to, a length of less than 100 residues, less than 200 residues, less than 300 residues, less than 400 residues, less than 500 residues, less than 800 residues or less than 1000 residues.

The invention also provides a bifunctional peptide or peptidomimetic which contains a homing peptide or peptidomimetic that selectively homes to tumor vasculature and selectively binds collagen fused to a second peptide or peptidomimetic having a separate function. The collagen can be, for example, non-helical collagen or collagen IV. Such bifunctional peptides and peptidomimetics have at least two functions conferred by different portions of the full-length molecule and can, for example, display anti-angiogenic activity or pro-apoptotic activity in addition to selective homing activity. As an exemplary bifunctional peptide, the invention provides CREKA-GG-$_D$(KLAKLAK)$_2$. In such a bifunctional peptide, the CREKA (SEQ ID NO: 1) portion exhibits selective homing activity, while the $_D$(KLAKLAK)$_2$ portion exhibits pro-apoptotic activity.

The present invention further provides an isolated multivalent peptide or peptidomimetic that includes at least two subsequences each independently containing the amino acid sequence CREKA (SEQ ID NO: 1), or a conservative variant or peptidomimetic thereof. The multivalent peptide or peptidomimetic can have, for example, at least three, at least five or at least ten of such subsequences each independently containing the amino acid sequence CREKA (SEQ ID NO: 1), or a conservative variant or peptidomimetic thereof. In particular embodiments, the multivalent peptide or peptidomimetic has two, three, four, five, six, seven, eight, nine, ten, fifteen or twenty identical or non-identical subsequences containing the amino acid sequence CREKA (SEQ ID NO: 1), or a conservative variant or peptidomimetic thereof. In a further embodiment, the multivalent peptide or peptidomimetic contains identical subsequences, which consist of the amino acid sequence SEQ ID NO: 1, or a conservative variant or peptidomimetic thereof. In a further embodiment, the multivalent peptide or peptidomimetic contains contiguous identical or non-identical subsequences, which are not separated by any intervening amino acids. In yet further embodiments, the multivalent peptide or peptidomimetic is cyclic or otherwise conformationally constrained.

Thus, the invention provides peptides and peptidomimetics, including bifunctional and multivalent peptides and peptidomimetics, and homing peptides and peptidomimetics discussed further below. As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective homing activity of the peptide upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^\alpha$—$C^\alpha$ cyclized amino acid; an $N^\alpha$-methylated amino acid; a β- or γ-amino cycloalkane carboxylic acid; an α,β-unsaturated amino acid; a β,β-dimethyl or β-methyl amino acid; a β-substituted-2,3-methano amino acid; an N—$C^\delta$ or $C^\alpha$—$C^\delta$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., *Acta Crystalloqr*. Section B, 35:2331 (1979)). This structural depository is continually updated as new crystal structures are determined and can be screened for compounds having suitable shapes, for example, the same shape as a peptide of the invention, as well as potential geometrical and chemical complementarity to a target molecule. Where no crystal structure of a peptide of the invention or a target molecule that binds the peptide is available, a structure can be generated using, for example, the program CONCORD (Rusinko et al., *J. Chem. Inf. Comput. Sci.* 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide of the invention, for example, with activity in selectively homing to tumor vasculature and selectively binding to collagen.

If desired, an isolated peptide or peptidomimetic of the invention, or a homing molecule of the invention as discussed further below, can be cyclic or otherwise conformationally constrained. As used herein, a "conformationally constrained" molecule, such as a peptide or peptidomimetic, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further below.

As used herein in reference to a peptide or peptidomimetic, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide or peptidomimetic also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl)benzoic acid (Mamb). Cyclization additionally can-be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide or peptidomimetic of the invention.

The present invention also provides a conjugate containing a therapeutic agent linked to a homing molecule that selectively homes to tumor vasculature and selectively binds collagen. In one embodiment, the invention provides a conjugate containing a homing molecule that selectively homes to breast tumor vasculature and that selectively binds collagen. In another embodiment, the invention provides a conjugate containing a homing molecule that selectively homes to tumor vasculature and that selectively binds non-helical collagen. In still another embodiment, the invention provides a conjugate containing a homing molecule that selectively homes to tumor vasculature and that selectively binds collagen IV. In a further embodiment, the invention provides a conjugate containing a homing molecule that selectively homes to tumor vasculature and that selectively binds denatured collagen IV in preference to native collagen IV. In a further embodiment, the invention provides a conjugate containing a homing molecule that selectively homes to tumor vasculature and that selectively binds the alpha 2 chain of collagen IV. In yet a further embodiment, the invention provides a conjugate containing a homing molecule that selectively homes to tumor vasculature and selectively binds collagen and which is not an antibody or antigen-binding fragment thereof.

The invention further provides a conjugate containing a tumor homing peptide or other homing molecule that selectively homes to tumor vasculature, where the homing molecule selectively binds a polypeptide or fragment thereof containing Gly-X-Y repeats. In another embodiment, the invention provides a conjugate containing a tumor homing peptide or other homing molecule that selectively homes to tumor vasculature, where the homing molecule selectively binds collagen or a fragment thereof containing Gly-X-Y repeats. In a further embodiment, the invention provides a conjugate containing a tumor homing peptide or other homing molecule that selectively homes to tumor vasculature, where the homing molecule selectively binds collagen IV or a fragment thereof, such as a fragment containing Gly-X-Y repeats.

The present invention is directed, in part, to the discovery that a collagen IV alpha-2 chain related polypeptide can act as a receptor for the CREKA (SEQ ID NO: 1) tumor homing peptide. Collagens are a major component of the extracellular matrix (ECM), an interconnected molecular network providing mechanical support for cells and tissues and regulating biochemical and cellular processes such as adhesion, migration, gene expression and differentiation (Timpl and Brown, *Bioessays* 18:123-132 (1995); Timpl, *Curr. Opin. Cell Biol.* 8:618-624 (1996); Herbst et al., *J. Cell Biol.* 106:1365-1373 (1998); Tsai, *Trends Cell Biol.* 8:192-195 (1998); and Dogic et al., *Curr. Topics Pathol.* 93:75-83 (1999)). In higher animals, at least 19 distinct collagen types differing in their higher order structures and functions have been identified based on the presence of the characteristic collagen triple-helix structure. In addition, at least 15 other proteins containing collagenous domains have been identified; such proteins include C1q and MSR (Hoppe and Reid, *Prot. Sci.* 3:1143-1158 (1994); and Myllyharju and Kivirikko, *Ann. Med.* 33:7 (2001)). The collagens are sometimes categorized into the fibrillar and nonfibrillar collagens. The fibrillar (interstitial) collagens include types I, II, III, V and XI, while the non-fibrillar collagens include types IV, VI, IX, X, XI, XII, XIV and XIII.

The amino acid sequence of collagen shows two unique features: (1) glycine is present as every third residue, generating a repeating $(Gly-X-Y)_n$ pattern and (2) a high proportion of residues (about 20%) are the imino acids proline and hydroxyproline (Brodsky and Ramshaw, *Matrix Biol.* 15:545-554 (1997)). See, for example, FIG. 7, which shows the sequence of the human collagen type IV α2 chain. The unique tertiary structure common to collagens consists of three parallel left-handed polyproline II-type strands wound around a common axis to form a triple helix with a shallow right-handed superhelical pitch. The packing of the collagen coiled-coil structure requires that every third residue be glycine, resulting in the repeated Gly-X-Y sequence characteristic of the collagens. The residue in the X position of the triplets is often L-proline, and the residue in the Y position is often 4(R)-hydroxy-L-proline (Jenkins and Raines, *Royal Soc. Chem.* 19:49-59 (2002)).

Collagen IV is a major component of the vascular basement membrane, which is a specialized form of the extracellular matrix that separates epithelia from its underlying mesenchyme and lines blood vessels (Hudson et al., *J. Biol. Chem.* 268:26033-26036 (1993); Timpl and Brown, supra, 1995; Timpl, supra, 1996). Type IV collagen plays a role in the interaction of basement membranes with cells, either directly or mediated by laminin or laminin/nidogen binding, and also binds heparin and heparan sulfate proteoglycans (Marneros and Olsen, *Matrix Biol.* 20:337-345 (2001)).

Six distinct genes encode the six type IV collagen chains denoted α1-α6(IV). The most widely expressed form of collagen IV, also known as "basement membrane collagen," is composed of two α1(IV) chains and one α2(IV) chain and is found in the basement membrane of virtually all blood vessels, while the α3-α6(IV) chains are found in specialized basement membranes such as the kidney glomerular basement membrane. α1(IV)$_2$α2(IV) trimers contain an "RGD" cell-binding site within the triple-helical domain; this site mediates binding by two integrin receptors: $\alpha_1\beta_1$ and $\alpha_2\beta_1$ (Messent et al., *J. Cell Sci.* 111:1127-1135 (1998); and Emsley et al., *Cell* 100:47-56 (2000)).

The individual chains of collagen type IV contain a cysteine-rich (7S) domain at the amino-terminus, a central triple-helical collagenous domain, and a carboxy-terminal non-collagenous (NC1) domain. Type IV collagen molecules form a network structure through covalently cross-linked and laterally associated 7S domains, end-to-end interactions of the NC1 domains and lateral association of the central collagenous domains. The most highly conserved portions of collagen IV are in the end regions: the globular NC1 domain at the carboxy-terminus, and the amino-terminal region of the triple helical domain. These evolutionarily conserved end regions have been shown to be important for the end-to-end aggregation of collagen IV chains. In contrast, the triple-helical domain of collagen IV molecules shows higher sequence variability. Non-triple-helical segments frequently interrupt the triple-helical domain, with the incidence of non-Gly-X-Y repeat segments generally higher in the amino-terminal half of the triple-helical domain than in the carboxy-terminal half.

The tumor homing molecules useful in the invention are characterized, in part, by the ability to selectively bind a collagen such as collagen IV. As used herein, the term "collagen" means a polypeptide containing Gly-X-Y repeats and that can form a triple helix of three parallel left-handed strands wound around a common axis to form a triple helix. Thus, the term collagen as used herein encompasses the individual component polypeptide chains that make up collagen as well as collagen in its native form. Collagens generally contain a high proportion of proline and hydroxyproline residues. A collagen can be a fibrillar or nonfibrillar collagen of any species, type or isofrom in native, denatured or partially denatured form. Thus, a homing molecule of the invention can selectively bind, without limitation, a mammalian collagen such as a human, bovine, rat or mouse collagen; any of a variety of types of collagen such as collagen type I, type II, type IV or type X; a collagen which, in its native state, includes one or more non-helical portions; and any of a variety of collagen isoforms including a collagen containing one or more α2 chains such as α2(IV) chains, for example, the α1(IV)$_2$α2(IV) is form of collagen type IV. The term collagen encompasses both native collagen as well as non-helical collagen. It is recognized that each of the conjugates and methods disclosed herein can be practiced, if desired, with a tumor homing molecule that selectively homes to tumor vasculature and selectively binds native collagen.

As used herein, the term "non-helical collagen" means a collagen that lacks triple helical structure in a portion or over the full-length of the molecule. Non-helical collagens include collagens which are partly or entirely non-helical such as, without limitation, native, wild type collagens containing non-helical portions; wild type collagens which are partly or entirely non-helical due to cleavage, modification by a kinase, protease or other enzyme, or interaction with one or more proteins which alter their structure; mutant forms of collagen; random-coiled collagens; and denatured collagens.

The term "collagen IV," as used herein, refers to a collagen that exhibits greater sequence similarity to the human collagen IV sequence SEQ ID NO: 4 shown in FIG. 7 than to another type of human collagen. A collagen IV can have, for example, greater than 40% amino acid identity with SEQ ID NO: 4, or can have, for example, greater than 50%, 60%, 70%, 80%, 90% or 95% identity with SEQ ID NO: 4.

As disclosed herein, CREKA (SEQ ID NO: 1) or another tumor homing molecule that selectively homes to tumor vasculature can bind collagen or a region or chain thereof and can exhibit enhanced binding to denatured or non-helical collagen as compared to native collagen. In one embodiment, the invention provides a conjugate containing CREKA (SEQ ID NO: 1) or another tumor homing molecule that selectively homes to tumor vasculature, where the homing molecule selectively binds a collagen or a region or chain thereof. In another embodiment, the invention provides a conjugate containing CREKA (SEQ ID NO: 1) or another tumor homing molecule that selectively homes to tumor vasculature, where the homing molecule selectively binds non-helical collagen or a non-helical region of a collagen. In another embodiment, the invention provides a conjugate containing CREKA (SEQ ID NO: 1) or another tumor homing molecule that selectively homes to tumor vasculature, where the homing molecule selectively binds collagen IV such as a non-helical region of collagen IV or denatured collagen IV. In a further embodiment, the invention provides a conjugate containing CREKA (SEQ ID NO: 1) or another tumor homing molecule that selectively homes to tumor vasculature, where the homing molecule selectively binds non-helical collagen or a non-helical region of collagen in preference to the corresponding collagen in its native helical form. In still a further embodiment, the invention provides a conjugate containing CREKA (SEQ ID NO: 1) or another tumor homing molecule that selectively homes to tumor vasculature, where the homing molecule selectively binds denatured collagen IV in preference to native, helical collagen IV. Where preferential binding is specified, the tumor homing molecule generally exhibits at least two-fold or more increased binding to the non-helical form of collagen as compared to the corresponding native collagen.

Similar to the enhanced binding to denatured collagen exhibited by the CREKA peptide SEQ ID NO: 1, a "cryptic" monoclonal antibody site can be exposed in collagen IV by proteolysis; this site is recognized by monoclonal antibody HUIV26 and has been associated with angiogenic blood vessels yet not with quiescent vessels (Xu et al., *J. Cell Biol.* 154:1069-1079 (2001)). In one embodiment, the invention provides a conjugate containing a homing molecule that selectively homes to tumor vasculature and selectively binds collagen and which is not monoclonal antibody HUIV26 or an antigen-binding fragment thereof. In another embodiment, the invention provides a conjugate containing a homing molecule that selectively homes to tumor vasculature and selectively binds collagen and which is not fibronectin or a fragment thereof, or an antibody or a fragment thereof. In a further embodiment, the invention provides a conjugate containing a homing molecule that selectively homes to tumor vasculature and selectively binds collagen and which is not fibronectin or a fragment thereof; an antibody or a fragment thereof; a collagenase or a fragment thereof, or a seminal fluid protein or a fragment thereof.

A variety of homing molecules that selectively home to tumor vasculature and selectively bind collagen such as non-helical collagen or collagen IV are useful in the conjugates of the invention. Such homing molecules include, without limitation, homing peptides and peptidomimetics. In one embodiment, the homing peptide or peptidomimetic portion of the conjugate has a length of at most 200 residues. In another embodiment, the homing peptide or peptidomimetic portion of the conjugate has a length of at most 50 residues. In a further embodiment, a conjugate of the invention contains a homing peptide or peptidomimetic that includes the amino acid sequence CREKA (SEQ ID NO: 1) or a conservative variant or peptidomimetic thereof. In another embodiment, a conjugate of the invention contains a homing peptide or peptidomimetic that includes the amino acid sequence CREKA (SEQ ID NO: 1) or a peptidomimetic thereof. In still a further embodiment, a conjugate of the invention contains a homing peptide that includes the amino acid sequence CREKA (SEQ ID NO: 1).

A variety of therapeutic agents-are useful in the conjugates of the invention including, without limitation, cancer chemotherapeutic agents, cytotoxic agents, anti-angiogenic agents, polypeptides, nucleic acid molecules and small molecules. As non-limiting examples, the invention provides a conjugate containing a therapeutic agent linked to a homing molecule that selectively homes to tumor vasculature and selectively binds collagen, where the therapeutic agent is a cancer chemotherapeutic agent, cytotoxic agent, anti-angiogenic agent, polypeptide, nucleic acid molecule or small molecule. As further non-limiting examples, the invention provides a conjugate containing a therapeutic agent linked to a homing peptide or peptidomimetic that selectively homes to tumor vasculature and selectively binds collagen, where the therapeutic agent is a cancer chemotherapeutic agent, cytotoxic agent, anti-angiogenic agent, polypeptide, nucleic acid molecule or small molecule. As additional non-limiting examples, the invention provides a conjugate that contains a therapeutic agent linked to a homing peptide or peptidomimetic containing the amino acid sequence CREKA (SEQ ID NO: 1), or a conservative variant or peptidomimetic thereof, that selectively homes to tumor vasculature and selectively binds collagen, where the therapeutic agent is a cancer chemotherapeutic agent, cytotoxic agent, anti-angiogenic agent, polypeptide, nucleic acid molecule or small molecule. Also provided herein is a conjugate that contains a therapeutic agent linked to a homing peptide or peptidomimetic containing the amino acid sequence CREKA (SEQ ID NO: 1), or a peptidomimetic thereof, that selectively homes to tumor vasculature and that selectively binds collagen, where the therapeutic agent is a cancer chemotherapeutic agent, cytotoxic agent, anti-angiogenic agent, polypeptide, nucleic acid molecule or small molecule. Further provided herein is a conjugate containing a therapeutic agent linked to a homing peptide containing the amino acid sequence CREKA (SEQ ID NO: 1) that selectively homes to tumor vasculature and selectively binds collagen, where the therapeutic agent is a cancer chemotherapeutic agent, cytotoxic agent, anti-angiogenic agent, polypeptide, nucleic acid molecule or small molecule. Any of these or other conjugates of the invention can optionally include a phage or other viral moiety.

The present invention further provides a method of directing a moiety to tumor vasculature in a subject by administering to the subject a conjugate which contains the moiety linked to a homing molecule that selectively homes to tumor vasculature and selectively binds collagen, thereby directing the moiety to tumor vasculature. In one embodiment, a method of the invention is practiced with a homing molecule that selectively homes to tumor vasculature and selectively binds non-helical collagen. In another embodiment, a method of the invention is practiced with a homing molecule that selectively homes to breast tumor vasculature and selectively binds collagen such as non-helical collagen. In yet another embodiment, a method of the invention is practiced with a homing molecule that selectively homes to tumor vasculature and selectively binds collagen IV. In still another embodiment, a method of the invention is practiced with a homing molecule that selectively homes to tumor vasculature and selectively binds denatured collagen IV in preference to native collagen IV. In a further embodiment, a method of the invention is practiced with a homing molecule that selectively homes to tumor vasculature and selectively binds the alpha 2 chain of collagen IV. In yet a further embodiment, a method of the invention is practiced with a homing molecule that selectively homes to tumor vasculature and selectively binds collagen and which is not an antibody or antigen-binding fragment thereof.

A variety of homing molecules can be useful in the methods of the invention for directing a moiety to tumor vasculature. Useful homing molecules include, yet are not limited to, homing peptides or peptidomimetics such as those including the amino acid sequence CREKA (SEQ ID NO: 1) or a conservative variant or peptidomimetic thereof. In one embodiment, a method of the invention for directing a moiety to tumor vasculature is practiced with a homing molecule that includes the amino acid sequence CREKA (SEQ ID NO: 1), or a peptidomimetic thereof. In a further embodiment, a method of the invention for directing a moiety to tumor vasculature is practiced with a homing molecule that includes the amino acid sequence CREKA (SEQ ID NO: 1). A variety of moieties can be targeted to tumor vasculature according to a method of the invention including, without limitation, therapeutic agents, detectable agents and phage. As non-limiting examples, therapeutic agents to be directed to tumor vasculature include cancer chemotherapeutic agents, cytotoxic agents, anti-angiogenic agents, polypeptides, nucleic acid molecules and small molecules.

The present invention additionally provides a method of reducing the number of tumor vessels in a subject by administering to the subject a conjugate which includes a therapeutic agent linked to a homing molecule that selectively homes to tumor vasculature and selectively binds collagen, thereby reducing the number of tumor vessels in the subject. A method of the invention can be useful, for example, for reducing the number of breast tumor vessels. In one embodiment, a method of the invention for reducing the number of tumor vessels is practiced with a homing molecule that selectively homes to tumor vasculature and selectively binds non-helical collagen. In another embodiment, a method of the invention for reducing the number of tumor vessels is practiced with a homing molecule that selectively homes to tumor vasculature and selectively binds collagen and which is not an antibody or antigen-binding fragment thereof. Homing molecules useful in the invention encompass, without limitation, homing peptides and peptidomimetics such as those including the amino acid sequence CREKA (SEQ ID NO: 1) or a conservative variant or peptidomimetic thereof. A method of the invention can be practiced, for example, with a homing peptide or peptidomimetic containing the amino acid sequence CREKA (SEQ ID NO: 1) or a peptidomimetic thereof. A method of the invention also can be practiced, for example, with a homing peptide containing the amino acid sequence CREKA (SEQ ID NO: 1). In a method of the invention for reducing the number of tumor vessels, a variety of therapeutic agents can be incorporated into the conjugate administered to the subject, including, for example, cancer chemotherapeutic agents, cytotoxic agents, and anti-angiogenic agents.

Also provided herein is a method of treating cancer in a subject by administering to the subject a conjugate which contains a therapeutic agent linked to a homing molecule that selectively homes to tumor vasculature and selectively binds collagen such as non-helical collagen or collagen IV. As a non-limiting example, a method of the invention can be useful for treating breast cancer. Homing molecules useful in the invention include those which selectively home to tumor vasculature and selectively bind collagen IV. Homing molecules useful in the invention further include those which selectively home to tumor vasculature and selectively bind the alpha 2 chain of collagen IV. In one embodiment, a method of the invention for treating cancer relies on a homing molecule that selectively homes to tumor vasculature and selectively binds collagen and which is not an antibody or antigen-binding fragment thereof.

A variety of homing molecules can be included in a conjugate useful for treating cancer according to a method of the invention. In one embodiment, a method of the invention is practiced with a conjugate that contains a homing peptide or peptidomimetic. In another embodiment, a method of the invention is practiced with a conjugate in which the peptide or peptidomimetic portion of the conjugate has a length of at most 200 residues. In another embodiment, a method of the invention is practiced with a conjugate in which the peptide or peptidomimetic portion of the conjugate has a length of at most 50 residues. In yet another embodiment, a method of the invention is practiced with a conjugate which contains a homing peptide or peptidomimetic that includes the amino acid sequence CREKA (SEQ ID NO: 1) or a conservative variant or peptidomimetic thereof. In still another embodiment, a method of the invention is practiced with a conjugate containing a homing peptide or peptidomimetic that includes the amino acid sequence CREKA (SEQ ID NO: 1), or a peptidomimetic thereof. In a further embodiment, a method of the invention is practiced with a conjugate containing a homing peptide which includes the amino acid sequence CREKA (SEQ ID NO: 1). A conjugate useful for treating cancer according to a method of the invention incorporates a therapeutic agent such as, without limitation, a cancer chemotherapeutic agent, cytotoxic agent, anti-angiogenic agent, polypeptide, nucleic acid molecule or small molecule and can optionally include one or more additional components such as a phage or other viral moiety.

The methods of the invention can be useful for treating a variety of cancers including, but not limited to, breast cancer, ovarian cancer, brain cancer such as glioblastoma or neuroblastoma, colon cancer, renal cancer, lung cancer, bladder cancer, prostate cancer and melanoma. Cancers can be treated at early or late stage and at a pre- or post-metastatic stage. It is understood that the conjugates of the invention can be part of combination therapy, where the conjugates are simultaneously or sequentially administered with one or more other anti-cancer therapeutics.

Exemplified herein is a homing molecule which selectively homes to the matrix of breast tumor vasculature but which does not detectably home to non-tumor vasculature such as brain, heart, kidney, lung, pancreatic and breast vasculature. Additional homing molecules that, like CREKA (SEQ ID NO: 1) selectively home to tumor vasculature such as breast tumor vasculature can be identified using in vivo panning as described in U.S. Pat. No. 5,622,699 coupled, if desired, with ex vivo selection or can be identified through in vitro assays such as the ability to selectively bind collagen as disclosed herein in Example III.

As used herein, the term "molecule" is used broadly to mean a polymeric or non-polymeric organic chemical such as a small molecule drug; a nucleic acid molecule such as an RNA, a DNA such as a cDNA or oligonucleotide; a peptide or peptidomimetic; or a protein such as a growth factor receptor or an antibody or fragment thereof such as an Fv, Fd, or Fab fragment or another antibody fragment containing the antigen-binding domain.

The term "homing molecule" as used herein, means any molecule that selectively homes in vivo to the vasculature of one or more tumors in preference to normal vasculature. Similarly, the term "homing peptide" or "homing peptidomimetic" means a peptide or peptidomimetic that selectively homes in vivo to the vasculature of one or more tumors in preference to normal vasculature. It is understood that a homing molecule that selectively homes in vivo to tumor vasculature can home to the vasculature of all tumors or can exhibit preferential homing to the vasculature of one or a subset of tumor types.

By "selectively homes" is meant that, in vivo, the homing molecule binds preferentially to tumor vasculature, such as breast tumor vasculature, as compared to non-tumoral vasculature. Such a homing molecule can selectively home, for example, to the matrix of tumor vasculature. Selective homing generally is characterized by at least a two-fold greater localization within tumor vasculature, such as breast tumor vasculature, as compared to several tissue types of non-tumor vasculature. A homing molecule can be characterized by 5-fold, 10-fold, 20-fold or more preferential localization to tumor vasculature as compared to several or many tissue types of non-tumoral vasculature, or as compared to-most or all non-tumoral vasculature. Thus, it is understood that, in some cases, a homing molecule homes, in part, to the vasculature of one or more normal organs in addition to homing to breast and other tumor vasculature.

In one embodiment, a conjugate of the invention includes a homing molecule that selectively homes to tumor vasculature and selectively binds collagen and which is not an antibody or antigen-binding fragment thereof. The term "antibody" is an art-recognized term that refers to a peptide or polypeptide containing one or more complementarity determining regions (CDRs). See, for example, Borrabaeck, *Antibody Engineering* 2nd Edition, Oxford University Press, New York (1995).

In another embodiment, the peptide or peptidomimetic portion of the conjugate has a defined length. The peptide or peptidomimetic portion of the conjugate can have, for example, a length of at most 10, 20, 30, 40, 50, 100, 150, 200, 250, 300, 400, 500, 600, 700, 800, 900, 1000 or 2000 residues. It is understood that the term "peptide or peptidomimetic portion of the conjugate" means total number of residues in the homing peptide or peptidomimetic and any contiguous protein component of the conjugate, such as a fused therapeutic protein or pro-apoptotic peptide.

The present invention also provides a conjugate containing a therapeutic agent and at least two homing molecules that each selectively homes to tumor vasculature and selectively binds collagen such as non-helical collagen or collagen IV. The two homing molecules can each independently contain, for example, the amino acid sequence CREKA (SEQ ID NO: 1) or a conservative variant or peptidomimetic thereof. Further provided by the invention is a conjugate containing a therapeutic agent and at least ten homing molecules that each selectively homes to tumor vasculature and selectively binds collagen such as non-helical collagen or collagen IV. The ten homing molecules can each independently contain, for example, the amino acid sequence CREKA (SEQ ID NO: 1) or a conservative variant or peptidomimetic thereof. The invention also provides a conjugate containing a therapeutic agent and at least 100 homing molecules that each selectively homes to tumor vasculature and selectively binds collagen such as non-helical collagen or collagen IV. The 100 homing molecules included in the conjugate can each independently contain, for example, the amino acid sequence CREKA (SEQ ID NO: 1) or a conservative variant or peptidomimetic thereof. Any of the above conjugates of the invention containing multiple homing molecules can optionally include a phage or other viral moiety.

A conjugate of the invention containing multiple homing molecules can include, for example, two or more, three or more, five or more, ten or more, twenty or more, thirty or more, forty or more, fifty or more, 100 or more, 200 or more, 300 or more, 400 or more, 500 or more, or 1000 or more homing molecules. In one embodiment, the conjugate includes homing molecules that all have an identical amino acid sequence. In another embodiment, the conjugate includes homing molecules having two or more non-identical amino acid sequences. Moieties useful in a conjugate of the invention incorporating multiple homing molecules include, without limitation, phage, retroviruses, adenoviruses, adeno-associated viruses and other viruses, cells, liposomes, polymeric matrices, non-polymeric matrices, particles such as gold particles, microdevices, nanodevices, and nano-scale semiconductor materials.

A conjugate of the invention can contain, for example, a liposome or other polymeric matrix linked to at least two homing molecules which each selectively homes to tumor vasculature and selectively binds collagen. If desired, the liposome or other polymeric matrix can be linked to at least ten, at least 100 or at least 1000 homing molecules which each selectively homes to tumor vasculature and selectively binds collagen. Homing molecules useful in such a conjugate can independently include, for example, the amino acid sequence CREKA (SEQ ID NO: 1), or a conservative variant or peptidomimetic of this sequence. Liposomes can be useful in such conjugates; liposomes consist of phospholipids or other lipids, are nontoxic, physiologically acceptable and metabolizable carriers that are relatively simple to make and administer (Gregoriadis, *Liposome Technology, Vol.* 1 (CRC Press, Boca Raton, Fla. (1984)). The liposome or other polymeric matrix can optionally include another component such as, without limitation, a therapeutic agent, cancer chemotherapeutic agent, cytotoxic agent, anti-angiogenic agent, polypeptide or nucleic acid molecule.

The present invention provides methods of directing a moiety to tumor vasculature. As used herein, the term "moiety" is used broadly to mean a physical, chemical, or biological material that generally imparts a biologically useful function to a linked molecule. A moiety can be any natural or nonnatural material including, without limitation, a biological material, such as a cell, phage or other virus; an organic chemical such as a small molecule; a radionuclide; a nucleic acid molecule or oligonucleotide; a polypeptide; or a peptide or peptidomimetic. Moieties useful in the invention include, yet are not limited to, therapeutic agents such as cancer chemotherapeutic agents, cytotoxic agents, pro-apoptotic agents, and anti-angiogenic agents; detectable labels and imaging agents; and tags or other insoluble supports. Moieties useful in the invention further include, without limitation, phage and other viruses, cells, liposomes, polymeric matrices, non-polymeric matrices or particles such as gold particles, microdevices and nanodevices, and nano-scale semiconductor materials. These and other moieties known in the art can be components of a conjugate of the invention.

In one embodiment, the moiety incorporated into a conjugate of the invention is a therapeutic agent. As used herein, the term "therapeutic agent" means a molecule which has one or more biological activities in a normal or pathologic tissue. A variety of therapeutic agents can be included in a conjugate of the invention. In one embodiment, a conjugate of the invention contains a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful in the conjugates of the invention. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., *J. Clin. Oncol.* 17:2341-2354 (1999), and Paridaens et al., *J. Clin. Oncol.* 18:724 (2000).

A cancer chemotherapeutic agent useful in a conjugate of the invention also can be an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, *Nature Biotechnology* 15:510 (1997); Steiner, In "Angiogenesis: Key principles-Science, technology and medicine," pp. 449-454 (eds. Steiner et al.; Birkhauser Verlag, 1992)), which can contribute to its effectiveness in treating cancer.

An alkylating agent such as melphalan or chlorambucil also can be a cancer chemotherapeutic agent useful in a conjugate of the invention. Similarly, a vinca alkaloid such as vindesine, vinblastine or vinorelbine; or an antimetabolite such as 5-fluorouracil, 5-fluorouridine or a derivative thereof can be a cancer chemotherapeutic agent useful in a conjugate of the invention.

A platinum agent also can be a cancer chemotherapeutic agent useful in the conjugates of the invention. Such a platinum agent can be, for example, cisplatin or carboplatin as described, for example, in Crown, *Seminars in Oncol.* 28:28-37 (2001). Other cancer chemotherapeutic agents useful in a conjugate of the invention include, without limitation, methotrexate, mitomycin-C, adriamycin, ifosfamide and ansamycins.

A cancer chemotherapeutic agent for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a conjugate of the invention for treatment of breast cancer (Fisher et al., *J. Natl. Cancer Instit.* 90:1371-1388 (1998)).

A therapeutic agent useful in a conjugate of the invention can be an antibody such as a humanized monoclonal antibody. As an example, the anti-epidermal growth factor receptor 2 (HER2) antibody, trastuzumab (Herceptin; Genentech, South San Francisco, Calif.) is a therapeutic agent useful in a conjugate of the invention for treating HER2/neu overexpressing breast cancers (White et al., *Annu. Rev. Med.* 52:125-141 (2001)).

A therapeutic agent useful in the invention also can be a cytotoxic agent, which, as used herein, is any molecule that directly or indirectly promotes cell death. Cytotoxic agents useful in the invention include, without limitation, small molecules, polypeptides, peptides, peptidomimetics, nucleic acid-molecules, cells and viruses. As non-limiting examples, cytotoxic agents useful in the invention include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, ricinus communis toxin (ricin); and cytotoxic cells such as cytotoxic T cells. See, for example, Martin et al., *Cancer Res.* 60:3218-3224 (2000); Kreitman and Pastan, *Blood* 90:252-259 (1997); Allam et al., *Cancer Res.* 57:2615-2618 (1997); and Osborne and Coronado-Heinsohn, *Cancer J. Sci. Am.* 2:175 (1996). One skilled in the art understands that these and additional cytotoxic agents described herein or known in the art can be useful in the conjugates and methods of the invention.

In one embodiment, a therapeutic agent is a therapeutic polypeptide. As used herein, a therapeutic polypeptide is any polypeptide with a biologically useful function. Therapeutic polypeptides useful in the invention encompass, without limitation, cytokines, antibodies, cytotoxic polypeptides; pro-apoptotic polypeptides; and anti-angiogenic polypeptides. As non-limiting examples, a therapeutic polypeptide useful in the invention can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon α (IFN-α); interferon γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art (see below). It is understood that these and other polypeptides with biological activity can be a "therapeutic polypeptide" useful in the invention.

A therapeutic agent useful in a conjugate of the invention also can be an anti-angiogenic agent. As used herein, the term "anti-angiogenic agent" means a molecule that reduces or prevents angiogenesis, which is the growth and development of blood vessels. A variety of anti-angiogenic agents are useful in the invention and can be prepared by routine methods. Such anti-angiogenic agents include, without limitation, small molecules; proteins such as dominant negative forms of angiogenic factors, transcription factors and antibodies; peptides and peptidomimetics; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, *Crit. Rev. Oncol. Hematol.* 34:89-110 (2000), and Kirsch et al., *J. Neurooncol.* 50:149-163 (2000).

Vascular endothelial growth factor (VEGF) has been shown to be important for angiogenesis in many types of cancer, including breast cancer angiogenesis in vivo (Borgstrom et al., *Anticancer Res.* 19:4213-4214 (1999)). The biological effects of VEGF include stimulation of endothelial cell proliferation, survival, migration and tube formation, and regulation of vascular permeability. An anti-angiogenic agent useful in the invention can be, for example, an inhibitor or neutralizing antibody that reduces the expression or signaling of VEGF or another angiogenic factor, for example, an anti-VEGF neutralizing monoclonal antibody (Borgstrom et al., supra, 1999). An anti-angiogenic agent also can inhibit another angiogenic factor such as a member of the fibroblast growth factor family such as FGF-1 (acidic), FGF-2 (basic), FGF-4 or FGF-5 (Slavin et al., *Cell Biol. Int.* 19:431-444 (1995); Folkman and Shing, *J. Biol. Chem.* 267:10931-10934 (1992)) or an angiogenic factor such as angiopoietin-1, a factor that signals through the endothelial cell-specific Tie2 receptor tyrosine kinase (Davis et al., *Cell* 87:1161-1169

(1996); and Suri et al., *Cell* 87:1171-1180 (1996)), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents useful in the invention including, without limitation, angiostatin; a kringle peptide of angiostatin; endostatin; anastellin, heparin-binding fragments of fibronectin; modified forms of antithrombin; collagenase inhibitors; basement membrane turnover inhibitors; angiostatic steroids; platelet factor 4 and fragments and peptides thereof; thrombospondin and fragments and peptides thereof; and doxorubicin (O'Reilly et al., *Cell* 79:315-328 (1994)); O'Reilly et al., *Cell* 88:277-285 (1997); Homandberg et al., *Am. J. Path.* 120:327-332 (1985); Homandberg et-al., *Biochim. Biophys. Acta* 874:61-71 (1986); and O'Reilly et al., *Science* 285:1926-1928 (1999)). Commercially available anti-angiogenic agents useful in the invention include, for example, angiostatin, endostatin, metastatin and 2ME2 (EntreMed; Rockville, Md.); anti-VEGF antibodies such as Avastin (Genentech; South San Francisco, Calif.); and VEGFR-2 inhibitors such as SU5416, a small molecule inhibitor of VEGFR-2 (SUGEN; South San Francisco, Calif.) and SU6668 (SUGEN), a small molecule inhibitor of VEGFR-2, platelet derived growth factor and fibroblast growth factor I receptor. It is understood that these and other anti-angiogenic agents can,be prepared by routine methods and are encompassed by the term "anti-angiogenic agent" as used herein.

A therapeutic agent useful in the invention also can be an antimicrobial peptide. Thus, the invention further provides a conjugate in which a homing molecule that selectively homes to tumor vasculature and selectively binds collagen is linked to an antimicrobial peptide, where the conjugate is selectively internalized by tumor vasculature and exhibits a high toxicity to the tumor vasculature, and where the antimicrobial peptide has low mammalian cell toxicity when not linked to the homing molecule. As used herein, the term "antimicrobial peptide" means a naturally occurring or synthetic peptide having antimicrobial activity, which is the ability to kill or slow the growth of one or more microbes and which has low mammalian cell toxicity when not linked to a homing molecule. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic α-helical structure (see U.S. Pat. No. 5,789,542; Javadpour et al., *J. Med. Chem.* 39:3107-3113 (1996); and Blondelle and Houghten, *Biochem.* 31: 12688-12694 (1992)). An antimicrobial peptide also can be, for example, a β-strand/sheet-forming peptide as described in Mancheno et al., *J. Peptide Res.* 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, *Biopolymers* 37:105-122 (1995); Alvarez-Bravo et al., *Biochem. J.* 302:535-538 (1994); Bessalle et al., *FEBS* 274:151-155 (1990).); and Blondelle and Houghten in Bristol (Ed.), *Annual Reports in Medicinal Chemistry* pages 159-168 Academic Press, San Diego). An antimicrobial peptide also can be an analog of a natural peptide, especially one that retains or enhances amphipathicity (see below).

An antimicrobial peptide incorporated into a conjugate of the invention has low mammalian cell toxicity when not linked to a tumor homing molecule. Mammalian cell toxicity readily can be assessed using routine assays. As an example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 µM for lytic activity, preferably concentrations greater than 200, 300, 500 or 1000 µM.

In one embodiment, the invention provides a conjugate in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art. $_D$(KLAKLAK)$_2$, for example, is an antimicrobial peptide which induces marked mitochondrial swelling at a concentration of 10 µM, significantly less than the concentration required to kill eukaryotic cells.

An antimicrobial peptide that induces significant mitochondrial swelling at, for example, 50 µM, 40 µM, 30 µM, 20 µM, 10 µM, or less, is considered a peptide that promotes disruption of mitochondrial membranes.

An antimicrobial peptide can include, for example, the sequence (KLAKLAK)$_2$ (SEQ ID NO: 20), (KLAKKLA)$_2$ (SEQ ID NO: 21), (KAAKKAA)$_2$ (SEQ ID NO: 22), or (KLGKKLG)$_3$ (SEQ ID NO: 23), and, in one embodiment, includes the sequence $_D$(KLAKLAK)$_2$. A conjugate of the invention, which contains a homing molecule that selectively homes to tumor vasculature and selectively binds collagen linked to an antimicrobial peptide, can have, for example, the sequence CREKA-GG-$_D$(KLAKLAK)$_2$.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, *Proteins: Structures and Molecular Properties* W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., *Biochim. Biophys. Acta* 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., *Biopolymers* 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic α-helical structure generally has an equivalent number of polar and nonpolar residues within the amphipathic domain and a sufficient number of basic residues to give the peptide an overall positive charge at neutral pH (Saberwal et al., *Biochim. Biophys. Acta* 1197: 109-131 (1994)). One skilled in the art understands that helix-promoting amino acids such as leucine and alanine can be advantageously included in an antimicrobial peptide of the invention (see, for example, Creighton, supra, 1984). Synthetic, antimicrobial peptides having an amphipathic α-helical structure are known in the art, for example, as described in U.S. Pat. No. 5,789,542 to McLaughlin and Becker.

It is understood by one skilled in the art of medicinal oncology that these and other agents are useful therapeutic agents, which can be used separately or together in the conjugates and methods of the invention. Thus, it is understood that a conjugate of the invention can contain one or more of such therapeutic agents and that additional components can be included as part of the conjugate, if desired. As a non-limiting example, it can be desirable in some cases to utilize an oligopeptide spacer between the homing molecule and the therapeutic agent (Fitzpatrick and Garnett, *Anticancer Drug Des.* 10:1-9 (1995)).

A variety of routes of administration are useful in the methods of the invention. Such routes include both systemic and local administration and encompass, without limitation, oral administration, intravenous injection, intraperitoneal injection, intramuscular injection, subcutaneous injection, transdermal diffusion or electrophoresis, local injection; extended release delivery devices such as locally implanted extended release devices and bioerodible or reservoir-based implants.

Also provided herein is a method of imaging tumor vasculature in a subject by (a) administering to the subject a conjugate containing a detectable agent linked to a homing molecule that selectively homes to tumor vasculature and selectively binds collagen; and (b) detecting the conjugate, thereby imaging tumor vasculature. In one embodiment, an imaging method of the invention is practiced with a homing molecule that selectively homes to tumor vasculature and selectively binds non-helical collagen. In another embodiment, an imaging method of the invention is practiced with a homing molecule that selectively homes to tumor vasculature and selectively binds collagen IV. In yet a further embodiment, an imaging method of the invention is practiced with a homing molecule that selectively homes to tumor vasculature and selectively binds denatured collagen IV in preference to native collagen IV. In another embodiment, an imaging method of the invention is practiced with a homing molecule that selectively homes to tumor vasculature and selectively binds collagen and which is not an antibody or antigen-binding fragment thereof. In another embodiment, a method of the invention is used to image breast tumor vasculature.

A variety of homing molecules can be useful in the imaging methods of the invention, including homing peptides and peptidomimetics such as homing peptides or peptidomimetics containing the amino acid sequence CREKA (SEQ ID NO: 1) or a conservative variant or peptidomimetic thereof. In one embodiment, the invention provides an imaging method that relies on a homing peptide or peptidomimetic containing the amino acid sequence CREKA (SEQ ID NO: 1) or a peptidomimetic thereof. In another embodiment, the invention provides an imaging method that relies on a homing peptide containing the amino acid sequence CREKA (SEQ ID NO: 1). Detectable agents useful in the imaging methods of the invention encompass, yet are not limited to, fluorophores and radionuclides, including radionuclides such as indium-111, technetium-99, carbon-11 and carbon-13.

The methods of the invention for imaging tumor vasculature can be useful for detecting the presence of tumor vasculature associated with a variety of tumors, including breast, ovarian, brain, colon, kidney, lung, bladder and prostate tumors and melanomas. Following administration of a conjugate of the invention containing a detectable agent, tumor vasculature is visualized. If the image is positive for the presence of tumor blood vessels, the tumor can be evaluated for size and quantity of vascular infiltration. These results provide valuable information to the clinician with regard to the stage of development of the cancer and the presence or probability of metastasis.

In a method of imaging tumor lymphatic vasculature, the conjugate administered contains a detectable agent that allows detection or visualization of vasculature in and around tumors, for example in and around breast tumors. For in vivo diagnostic imaging of tumor vasculature, a homing molecule is linked to a detectable agent that, upon administration to the subject, is detectable external to the subject. Such a detectable agent can be, for example, a gamma ray emitting radionuclide such as indium-113, indium-115 or technetium-99; following administration to a subject, the conjugate can be visualized using a solid scintillation detector.

A variety of detectable agents are useful in the methods of the invention. As used herein, the term "detectable agent" refers to any molecule which can be administered in vivo and subsequently detected. Detectable agents useful in the conjugates and imaging methods of the invention include yet are not limited to radiolabels and fluorescent molecules. Exemplary radionuclides include indium-111, technetium-99, carbon-11, and carbon-13. Fluorescent molecules useful in the invention encompass, without limitation, fluorescein, allophycocyanin, phycoerythrin, rhodamine, and Texas red.

As disclosed herein, peptide SEQ ID NO: 1 recognizes a receptor expressed in the matrix of tumor blood vessels and thereby selectively homes to the matrix of tumor vasculature. Furthermore, the matrix protein recognized by SEQ ID NO: 1 does not serve as a receptor for significant homing to the vasculature of a variety of normal tissues including brain, heart, kidney, lung and pancreas. The binding of SEQ ID NO: 1 to a target receptor expressed in the matrix of tumor vasculature forms the basis for the selective homing activity of peptide SEQ ID NO: 1 and related peptides, peptidomimetics and other molecules. Based on this discovery, it is clear that molecules structurally unrelated to SEQ ID NO: 1 but which also bind the same target receptor also have the same characteristic of selective homing to tumor vasculature. Such molecules can be identified by the ability to selectively bind to, or compete for binding to, collagen IV or another collagen or fragment bound by SEQ ID NO: 1. Thus, the invention provides conjugates containing a molecule that selectively binds collagen IV or another collagen or other receptor bound by peptide SEQ ID NO: 1; such a molecule also is characterized by the ability to selectively home to tumor vasculature. In one embodiment, the invention provides a conjugate containing a homing peptide or peptidomimetic having a length of at most 4, 5, 6, 7, 8, 9, 10, 15, 20, 40, 60 or 100 residues, that specifically binds denatured collagen IV or another receptor bound by peptide SEQ ID NO: 1.

The present invention further provides a method of identifying a tumor homing molecule that selectively homes to tumor vasculature by contacting a substantially purified collagen, or fragment thereof, with one or more molecules; and determining specific binding of a molecule to the substantially purified collagen or fragment thereof, where the presence of specific binding identifies the molecule as a tumor homing molecule that selectively homes to tumor vasculature. A method of the invention can further include, if desired, the steps of administering the collagen binding molecule in vivo; and determining binding of the collagen binding molecule to tumor vasculature. If desired, the substantially purified collagen useful in the invention can be immobilized on a support.

Substantially purified collagens useful in the invention include, yet are not limited to, collagen type I, II, IV and X and further include, without limitation, any collagen alpha 2 chain. In one embodiment, a screening method of the invention is practiced with a substantially purified non-helical collagen, or fragment thereof. In another embodiment, a screening method of the invention is practiced with substantially purified collagen or fragment thereof which is denatured, for example, by boiling. In a further embodiment, a screening method of the invention is practiced with substantially purified collagen type IV or a fragment thereof. The method can be practiced, for example, with denatured collagen type IV, or a fragment thereof, or with the alpha 2 chain of collagen type IV or a fragment thereof. As a non-limiting example, a method of the invention can be practiced with substantially purified collagen IV which is denatured by boiling.

The methods of the invention can be practiced with any species, type or isoform of collagen including those described herein above, and further can be practiced with any fragment of collagen which contains Gly-X-Y repeats or which can selectively bind CREKA (SEQ ID NO: 1). Thus, substantially purified collagen useful in the screening methods of the invention include, without limitation, mammalian collagens such as human, bovine, rat and mouse collagens; various types of collagen including collagen type I, type II, type IV and type X; and various collagen isoforms including a collagen containing one or more α2 chains such as α2(IV) chains. Substantially purified collagens useful in the invention include those purified from normal tissue or tumor sources as well as recombinant polypeptides and can be prepared by routine methods.

Collagen fragments also can be useful in the screening methods of the invention. Such fragments encompass fragments that include Gly-X-Y repeats, for example, fragments of a collagen alpha 2 chain. In one embodiment, a collagen fragment useful in the invention is homologous to residues 338 to 476 of the human collagen IV alpha 2 chain shown in FIG. 7. Such a fragment can have, for example, greater than 40%, 50%, 60%, 70%, 80%, 90% or 95% identity with residues 338 to 476 of SEQ ID NO: 4. It is understood that these and other fragments that retain selective binding for the CREKA (SEQ ID NO: 1) peptide are useful in the screening methods of the invention.

The present invention further provides a method of identifying a tumor homing molecule that selectively homes to tumor vasculature by contacting a substantially purified polypeptide containing Gly-X-Y repeats, or a fragment thereof, with one or more molecules; and determining specific binding of a molecule to the substantially purified polypeptide or fragment thereof, where the presence of specific binding identifies the molecule as a tumor homing molecule that selectively homes to tumor vasculature. A method of the invention can further include, if desired, the steps of administering the polypeptide binding molecule in vivo; and determining binding of the molecule to tumor vasculature. In one embodiment, the substantially purified polypeptide or fragment thereof is homologous to SEQ ID NO: 2. In another embodiment, the substantially purified polypeptide or fragment thereof is denatured, for example, by boiling.

The following examples are intended to illustrate but not limit the present invention.

EXAMPLE 1

Phage Expressing the Pentapeptide CREKA (SEQ ID NO: 1) Home to Breast Cancer Tissue This example describes identification of the CREKA (SEQ ID NO: 1) tumor homing peptide.

To identify phage that selectively home to tumor vasculature, a phage-displayed peptide library was injected intravenously into two month-old MMTV-PyMT mice; bound phage were subsequently recovered from breast tumor tissue. The number of phage recovered from breast tissue increased about 100-fold after three rounds of injection and recovery; additional rounds of injection and recovery did not further improve the selectivity. Sequence analysis showed that phage displaying the peptide CREKA (SEQ ID NO: 1) were significantly enriched in the phage pool recovered after three rounds of screening, representing about 20% of phage present in the pool.

Phage preparations ($1 \times 10^9$ plaque forming units (pfu)) of CREKA (SEQ ID NO: 1)-displaying phage were injected into tumor-bearing mice and subsequently recovered from breast tumors and a variety of normal tissues. As shown in FIG. 1A, CREKA (SEQ ID NO: 1) phage homed to breast tissue about 130 times more efficiently than non-recombinant T7 phage. The CREKA (SEQ ID NO: 1) phage also homed to the vasculature of MDA-MB-435 human breast cancer cell xenografts grown in the mammary fat pad of nude mice with a 20-fold specificity over non-recombinant phage as shown in FIG. 1B. The CREKA (SEQ ID NO: 1) phage did not home to a variety of normal tissues, including the pancreas, brain, kidneys and heart of MMTV PyMT tumor-bearing mice (see FIG. 1A). Furthermore, the CREKA (SEQ ID NO: 1)-displaying phage also did not home to the vasculature of small xenograft tumors growing in the mammary fat pad. Tumor homing of CREKA (SEQ ID NO: 1)-displaying phage was specific by the criterion of ligand inhibition; co-injection of synthetic free CREKA (SEQ ID NO: 1) peptide inhibited CREKA (SEQ ID NO: 1)-displaying phage recovery from breast cancer tissue while an excess of an unrelated control peptide did not inhibit homing of CREKA (SEQ ID NO: 1)-phage. Similarly, free CREKA (SEQ ID NO: 1) peptide also did not inhibit homing of phage displaying the control peptide.

A peptide library with the general structure of $CX_7C$, where C is cysteine and X is any amino acid, was constructed in T7 phage essentially as follows. Briefly, complementary oligonucleotides with NNK codons encoding a random peptide insert were annealed. The resulting double stranded DNA had 5' EcoRI and 3' HindIII overhangs, which were phosphorylated with T4 polynucleotide kinase (Novagen; Madison, Wis.) and ligated into 1 µg of T7Select415-1b vector arms (Novagen). The ligate was directly added to 50 µl of packaging extract and incubated for two hours. The total number of recombinants obtained was ~$10^8$ as measured by formation of plaque forming units. Recombinants were amplified in 500 ml of liquid culture; purification of phage particles 30 and sequencing of single stranded phage DNA was performed as described in Essler and Ruoslahti, *Proc. Natl. Acad. Sci., USA* 99:2252-2257 (1999). The source of all materials not specified in this and further examples was Sigma (St. Louis, Mo.).

In vivo phage display screens were performed with 65 to 75 day old transgenic MMTV PyMT mice obtained from Dr. William Muller. MDA-MB-435 tumors were generated as described in Laakkonen et al., *Nat. Med.* 7:751-755 (2002). Briefly, $10^6$ MDA-MB-435 cells in 100 µl phosphate buffered saline (PBS) were injected into the mammary fat pad of nude mice. Tumors were grown for five weeks before the animals were used in vivo studies. In vivo phage screening was performed as described in Porkka et al., *Proc. Natl. Acad. Sci., USA* 99:7444-7449 (2002), with a few modifications. Briefly, mice were anesthetized with avertin and then injected intravenously with $10^9$ pfu of the $CX_7C$ library. Mice were perfused through the heart with 10 ml of PBS seven minutes after the injection. Tumor tissue was then excised, weighed, and a cell suspension was made using a Medimachine (DAKO; Denmark). The resulting single cells were centrifuged at 1500 rpm and washed five times with 5 ml PBS. Cell-adherent phage particles were recovered by infecting BL21 bacteria (Novagen), and the number of phage quantified by plaque assay.

Synthetic CREKA (SEQ ID NO: 1) peptide was synthesized in the peptide synthesis facility at The Burnham Institute using Fmoc chemistry on a solid-phase synthesizer. The peptide was purified by HPLC, and the sequence and structure confirmed by mass spectrometry.

These results demonstrate that the CREKA (SEQ ID NO: 1) peptide confers on an attached moiety such as a phage the ability to be selectively directed in vivo to tumor vasculature.

EXAMPLE 2

Tissue Localization of CREKA (SEQ ID NO: 1)-Displaying Phage and CREKA (SEQ ID NO: 1) Peptide This example describes the selective homing of CREKA (SEQ ID NO: 1)-displaying phage and labeled CREKA (SEQ ID NO: 1) peptide.

Immunoperoxidase staining revealed CREKA (SEQ ID NO: 1) phage in MMTV PyMT tumors (FIG. 2A) and in MDA-MB-435 xenografts (FIG. 2B) 15 minutes after intravenous injection. In contrast, similarly injected non-recombinant T7 phage could not be detected in the tumors (FIG. 2C). Furthermore, the IgG control antibody staining was negative (FIG. 2D), and no CREKA (SEQ ID NO: 1)-displaying phage were detected in control normal organs such as the brain, kidney and heart (FIGS. 2E, 2F and 2G, respectively). The liver stained positive for the CREKA (SEQ ID NO: 1) phage as shown in panel 2H and also stained positive for control phage, indicating non-specific uptake of the phage by the reticuloendothelial system, as has been observed previously (Pasqualini et al., *Cancer Res.* 60:722-727 (2000)).

Similarly, fluorescein (FITC) and rhodamine labeled CREKA (SEQ ID NO: 1) peptides also were detected in MMTV PyMT tumors 15 minutes after intravenous injection but were not observed in normal tissues such as the brain or liver (compare FIG. 3A with FIGS. 3B and 3C). The peptides were found primarily in the tumor periphery 15 minutes after the injection but could be detected in the entire tumor after two hours, localizing outside the blood vessels as shown in FIG. 3D. As expected, control organs such as the heart, injected with rhodamine-labeled CREKA (SEQ ID NO: 1) and FITC-tomato-lectin, which stains blood vessels, were negative for CREKA (SEQ ID NO: 1) peptide staining (see FIG. 3F).

Immunohistochemical detection of phage was performed essentially as follows. Tumor-bearing mice were injected intravenously via the tail vein with $1 \times 10^9$ pfu CREKA (SEQ ID NO: 1) phage or non-recombinant T7 phage. After 15 minutes, the mice were perfused through the heart with 10 ml PBS. The indicated tissue was then dissected, fixed with 3.7% paraformaldehyde, and embedded in paraffin. Sections of 5 µm were cut, de-paraffinized, washed with water, and treated with 3% hydrogen peroxide for 30 minutes. Rabbit anti-T7 antibody (Oku et al., *Oncogene* 21:2262-2269 (2002)) was diluted 1:1000 and applied, and the slides were incubated for one hour at room temperature. Slides were washed three times with PBS and then incubated with anti-rabbit IgG (DAKO) followed by incubation with 3,3'-diaminobenzidine (DAB; Sigma) according to the instructions of the manufacturer. The slides were washed with water and counter-stained with hematoxylin.

Peptide synthesis and labeling of peptides with fluorescein and rhodamine was carried out as described in Wender et al., *Proc. Natl. Acad. Sci., USA* 97:13003-13008 (2000), and Oku et al., supra, 2002, and detected essentially as follows. A 1 mg/ml solution of fluorescein-labeled CREKA (SEQ ID NO: 1) peptide in PBS was injected into the tail vein of MMTV PyMT mice. After 15 minutes or two hours of circulation, mice were perfused through the heart with 10 ml PBS, and the indicated organs harvested. Tissues were dissected, fixed with 3.7% paraformaldehyde for two hours, washed with PBS, and soaked in glycine (0.01%, pH 7.4) for 12 hours. Specimens were then treated with a sucrose gradient (12%, 15%, 18%), embedded in Tissue-Tek© (Miles Inc.; Elkhardt, Ind.) and frozen. Subsequently, 5 µm sections were prepared for fluorescence microscopy, and 50 µm sections were prepared for confocal microscopy. To detect blood vessels, 100 µl of 1 mg/ml solution of fluorescein-labeled tomato lectin (Vector Labs; Burlingame, Calif.) was injected into mice in PBS.

These results demonstrate that CREKA (SEQ ID NO: 1)-displaying phage or labeled CREKA (SEQ ID NO: 1) peptide quickly localizes to the vasculature of human or murine breast tumors in preference to the vasculature of normal organs.

EXAMPLE 3

A Collagen IV Alpha-2 Chain-Related Protein Binds to the CREKA (SEQ ID NO: 1) Peptide This example describes identification of a receptor for the CREKA (SEQ ID NO: 1) tumor homing peptide.

A. Identification of a Receptor for the CREKA (SEQ ID NO: 1) Peptide

To identify a receptor for CREKA (SEQ ID NO: 1) in breast tumor vasculature, a mouse breast cancer cDNA library was screened for binding of expressed proteins to immobilized CREKA (SEQ ID NO: 1) peptide. Among the individual phage clones obtained, one clone avidly bound to the peptide-coated surface (FIG. 4A), but not to an uncoated surface treated with the blocking buffer only. Sequence analysis showed that this clone encodes a 138 amino acid fragment related to the collagen IV alpha-2 chain (see FIG. 4B). The presence of Gly-X-Y repeats revealed that the fragment was derived from the triple helical portion of collagen IV.

Expression cloning was performed essentially as described in Essler and Ruoslahti, *Proc. Natl. Acad. Sci., USA* 99:2252-2257 (2002). CREKA (SEQ ID NO: 1) peptide was synthesized on a Symphony synthesizer (Rainin Instruments; Emeryville, Calif.) at The Burnham Institute peptide facility, and purified by high performance liquid chromatography. The peptide showed the correct mass by MALDI-TOF mass spectroscopy and was greater than 95% pure. Biotin-labeled peptide (2 mg/ml) was immobilized on a streptavidin-coated 96 well Reacti-Bind® polystyrene strip plate (Pierce; Rockford, Ill.) by coating overnight at room temperature with 100 µl of 2 mg/ml biotin-CREKA (SEQ ID NO: 1) in PBS. The wells were subsequently treated three times with 200 µl SuperBlock® blocking buffer (Pierce).

A mouse breast carcinoma cDNA library from 4T1 cells obtained from the American Type Culture Collection (ATCC) was prepared as follows. RNA from 4T1 cells was purified using a RNeasy® kit (Qiagen; Valencia, Calif.), and mRNA was twice purified from the RNA using an Oligotex™ Direct mRNA kit (Qiagen). Random-primed cDNA synthesis was performed using an OrientExpress™ cDNA synthesis kit (Novagen). The cDNAs were ligated into a modified T7Select1-2b phage vector (Novagen) between the 3' end of the T7 10B coat protein gene and the 5' end of nucleic acid sequence encoding a myc epitope in all three reading frames. The phage vector ligation products were packaged using a commercial packaging extract (Novagen) and amplified by infecting a BLT 5615 bacterial culture. The library diversity was $1.2 \times 10^8$ as determined by a phage colony plaque assay. Phage clones that contained cDNA inserts without stop codons were isolated by sorting with monoclonal anti-myc antibodies (Chemicon; Temecula, Calif.) coated onto magnetic beads (Miltenyi Biotec; Auburn, Calif.) Phage clones that bound to the anti-myc antibody coated beads were recovered and amplified by infecting a BLT 5615 bacterial culture. Three rounds of myc antibody sorting were performed. Over 90% of the phage clones from a random sampling were found to contain open reading frame cDNA inserts, and the phage clones expressed, on average, protein fragments that were 75 amino acids in length.

Binding assays were performed as follows. Phage suspension (100 µl, $10^6$ pfu/µl in PBS) was incubated in the 96 well Reacti-Bind® polystyrene strip plate for one hour, and the wells subsequently washed 20 times with 100 µl PBS. Phage bound to immobilized CREKA (SEQ ID NO: 1) peptide were eluted with an excess of cognate SEQ ID NO: 1 peptide by application of 100 µl of a 5 mg/ml solution of peptide SEQ ID NO: 1 in PBS. The phage were then recovered and amplified by infecting a BLT 5615 bacterial culture for 10 minutes at room temperature. Recovered phage were individually assayed for specific binding to CREKA (SEQ ID NO: 1) coated wells.

B. Binding of CREKA (SEQ ID NO: 1) to Collagen is Specific and is Enhanced by Denaturation As shown in FIG. 5A, the observed interaction between CREKA (SEQ ID NO: 1) and the collagen IV fragment SEQ ID NO: 2 was specific, as it could be inhibited by an excess of cognate CREKA (SEQ ID NO: 1) peptide in a dose dependent manner. Furthermore, as shown in FIG. 5B, rabbit anti-mouse collagen IV serum, but not control serum, blocked the interaction between the phage-displayed collagen fragment and immobilized CREKA (SEQ ID NO: 1). Fibronectin, which binds to various collagens in their non-triple helical form, did not significantly reduce binding of the CREKA (SEQ ID NO: 1)-displaying phage (FIG. 5B; see Engvall et al., supra, 1982).

CREKA (SEQ ID NO: 1)-displaying phage also were assayed for the ability to bind surfaces coated with collagens I, II, IV and X. As shown in FIG. 5C, the CREKA (SEQ ID NO: 1) phage bound to each of these collagens. Furthermore, denaturation of the collagens by boiling enhanced the CREKA (SEQ ID NO: 1)-phage binding, indicating that non-helical collagen can be a receptor for CREKA (SEQ ID NO: 1) in tumor vasculature. In agreement with in vivo binding of CREKA (SEQ ID NO: 1) to collagen, co-injection of gelatin, which is denatured collagen I, completely blocked in vivo tumor homing of CREKA (SEQ ID NO: 1)-expressing phage.

For competitions with free CREKA (SEQ ID NO: 1) peptide, phage displaying the clone #3 collagen IV fragment (SEQ ID NO: 2; $1 \times 10^7$ pfu) were applied to CREKA (SEQ ID NO: 1)-coated surfaces in 96-well ELISA plates prepared as described above, and incubated for one 20 hour in the presence of 0.01 mg, 0.05 mg, or 0.1 mg soluble CREKA (SEQ ID NO: 1) peptide in 100 µl PBS. In some experiments, phage were incubated with 100 pg/ml fibronectin (Roche; Germany); with rabbit anti-collagen IV serum diluted 1:30 in PBS with 1 mM MgCl$_2$ and CaCl$_2$; or with the same dilution of normal rabbit serum. After 20 washes with 100 µl PBS, phage particles were recovered by infecting BL21 bacteria, and the number of attached phage determined. Phage output was determined as a percentage of phage recovered from wells not treated with soluble peptide.

To test phage binding to immobilized collagen, 96 well ELISA plates were treated for 12 hours at room temperature with native or boiled collagen I from calf skin (Sigma), native or boiled collagen II from chicken cartilage (Sigma), native or boiled collagen IV from Engelbreth Holm Swarm tumors (Sigma) or native or boiled collagen X from human placenta (Sigma), each at 200 µg/ml in PBS. The plates were blocked with 200 µl of SuperBlock® blocking buffer. After washing of the plates, CREKA (SEQ ID NO: 1) phage ($1 \times 10^5$ pfu) were applied in each well and incubated for one hour. After washing with PBS, phage particles were recovered by infecting BL21 bacteria, and the number of pfu was determined as described above.

C. Localization of CREKA (SEQ ID NO: 1) Peptide and Collagen IV

Localization of collagen IV was compared to the localization of CREKA (SEQ ID NO: 1) peptide in breast tumors. As shown in FIG. 6, FITC-CREKA (SEQ ID NO: 1) partially co-localized with collagen IV in connective tissue surrounding individual tumor masses in MMTV-PyMT mice. A FITC-labeled control peptide did not co-localize with collagen IV in MMTV-PyMT tumors. These results are consistent with a role for collagen IV as a receptor for the CREKA (SEQ ID NO: 1) peptide in tumor vasculature.

Immunostaining was performed after injection of 100 µg FITC-CREKA (SEQ ID NO: 1) into the tail vein of MMTV PyMT mice. After 15 minutes, tumors were dissected, fixed, stained for collagen IV and counter-stained with DAPI essentially as follows. Collagen IV was detected by immunofluorescence as described in Engvall et al., supra, 1982, with the following modifications. Briefly, mouse tissues were fixed with 3.7% paraformaldehyde for two hours, washed with PBS, and incubated in glycine (0.01%, pH 7.4) for 12 hours to quench autofluorescence of the samples. Specimens were then treated with increasing concentrations of sucrose (12%, 15%, 18%), embedded in Tissue-Tek© (Miles Inc.), frozen, and cut into 5 μm sections. After an overnight incubation with rabbit antiserum to collagen IV (diluted 1:40 in PBS) at 4° C. (Engvall et al., supra, 1982), the sections were washed with PBS and incubated with rhodamine-labeled goat anti-rabbit antibody (DAKO) at a dilution of 1:30 for 30 minutes. After washing, the sections were mounted in 90% glycerol.

In sum, the results described in this example demonstrate that the CREKA (SEQ ID NO: 1) peptide binds a collagen IV α-2 chain related protein and further indicate that collagen IV or a related collagen can act as a receptor for tumor homing molecules in tumor vasculature.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. An isolated peptide comprising the amino acid sequence CREKA (SEQ ID NO: 1), said peptide having a length of less than 100 residues, wherein said peptide selectively homes to tumor vasculature.

2. The isolated peptide of claim 1, said peptide having a length of less than 50 residues.

3. The isolated peptide of claim 1, said peptide having a length of less than 40 residues.

4. The isolated peptide of claim 1, said peptide having a length of less than 35 residues.

5. The isolated peptide of claim 1, said peptide having a length of less than 30 residues.

6. The isolated peptide of claim 1, said peptide having a length of less than 25 residues.

7. The isolated peptide of claim 1, said peptide having a length of less than 20 residues.

8. The isolated peptide of claim 1, said peptide having a length of less than 15 residues.

9. The isolated peptide of claim 1, said peptide having a length of less than 12 residues.

10. The isolated peptide of claim 1, said peptide having a length of less than 10 residues.

11. The isolated peptide of claim 1, said peptide having a length of less than 9 residues.

12. The isolated peptide of claim 1, said peptide having a length of less than 8 residues.

13. The isolated peptide of claim 1, said peptide having a length of less than 7 residues.

14. The isolated peptide of claim 1, said peptide having a length of less than 6 residues.

15. An isolated peptide comprising the amino acid sequence CREKA (SEQ ID NO: 1), said peptide having a length of less than 100 residues, wherein said peptide selectively binds collagen.

16. The isolated peptide of claim 15, said peptide having a length of less than 50 residues.

17. The isolated peptide of claim 15, said peptide having a length of less than 40 residues.

18. The isolated peptide of claim 15, said peptide having a length of less than 35 residues.

19. The isolated peptide of claim 15, said peptide having a length of less than 30 residues.

20. The isolated peptide of claim 15, said peptide having a length of less than 25 residues.
21. The isolated peptide of claim 15, said peptide having a length of less than 20 residues.
22. The isolated peptide of claim 15, said peptide having a length of less than 15 residues.
23. The isolated peptide of claim 15, said peptide having a length of less than 12 residues.
24. The isolated peptide of claim 15, said peptide having a length of less than 10 residues.
25. The isolated peptide of claim 15, said peptide having a length of less than 9 residues.
26. The isolated peptide of claim 15, said peptide having a length of less than 8 residues.
27. The isolated peptide of claim 15, said peptide having a length of less than 7 residues.
28. The isolated peptide of claim 15, said peptide having a length of less than 6 residues.
29. A conjugate comprising a moiety linked to a homing peptide comprising the amino acid sequence CREKA (SEQ ID NO: 1), wherein said homing peptide selectively homes to tumor vasculature.
30. The conjugate of claim 29, wherein said homing meleeide peptide selectively homes to breast tumor vasculature.
31. The conjugate of claim 29, wherein the peptide portion of said conjugate has a length of less than 50 residues.
32. The conjugate of claim 29, wherein the peptide portion of said conjugate has a length of less than 40 residues.
33. The conjugate of claim 29, wherein the peptide portion of said conjugate has a length of less than 35 residues.
34. The conjugate of claim 29, wherein the peptide portion of said conjugate has a length of less than 30 residues.
35. The conjugate of claim 29, wherein the peptide portion of said conjugate has a length of less than 25 residues.
36. The conjugate of claim 29, wherein the peptide portion of said conjugate has a length of less than 20 residues.
37. The conjugate of claim 29, wherein the peptide portion of said conjugate has a length of less than 15 residues.
38. The conjugate of claim 29, wherein the peptide portion of said conjugate has a length of less than 12 residues.
39. The conjugate of claim 29, wherein the peptide portion of said conjugate has a length of less than 10 residues.
40. The conjugate of claim 29, wherein the peptide portion of said conjugate has a length of less than 9 residues.
41. The conjugate of claim 29, wherein the peptide portion of said conjugate has a length of less than 8 residues.
42. The conjugate of claim 29, wherein the peptide portion of said conjugate has a length of less than 7 residues.
43. The conjugate of claim 29, wherein the peptide portion of said conjugate has a length of less than 6 residues.
44. The conjugate of claim 29, wherein said moiety is a therapeutic agent.
45. The conjugate of claim 44, wherein said therapeutic agent is a cancer chemotherapeutic agent.
46. The conjugate of claim 44, wherein said therapeutic agent is a cytotoxic agent.
47. The conjugate of claim 44, wherein said therapeutic agent is an anti-angiogenic agent.
48. The conjugate of claim 44, wherein said therapeutic agent is a polypeptide.
49. The conjugate of claim 29, wherein said moiety is a small molecule.
50. The conjugate of claim 29, wherein said moiety comprises a virus.
51. The conjugate of claim 50, wherein said virus is a phage.
52. The conjugate of claim 29, comprising at least two homing peptides that each selectively homes to tumor vasculature.
53. The conjugate of claim 52, wherein said at least two homing peptides each independently comprises the amino acid sequence CREKA (SEQ ID NO: 1).
54. The conjugate of claim 29, comprising at least ten homing peptides that each selectively homes to tumor vasculature.
55. The conjugate of claim 54, wherein said at least ten homing peptides each independently comprises the amino acid sequence CREKA (SEQ ID NO: 1).
56. The conjugate of claim 29, comprising at least 100 homing peptides that each selectively homes to tumor vasculature.
57. The conjugate of claim 56, wherein said at least 100 homing peptides each independently comprises the amino acid sequence CREKA (SEQ ID NO: 1).
58. The conjugate of claim 56, wherein said moiety comprises a virus.
59. The conjugate of claim 58, wherein said virus is a phage.
60. A conjugate comprising a moiety linked to a homing peptide comprising the amino acid sequence CREKA (SEQ ID NO: 1), wherein said homing peptide selectively binds collagen.
61. The conjugate of claim 60, wherein said homing peptide selectively binds non-helical collagen.
62. The conjugate of claim 60, wherein said homing peptide selectively binds collagen IV.
63. The conjugate of claim 62, wherein said homing peptide selectively binds denatured collagen IV in preference to native collagen IV.
64. The conjugate of claim 62, wherein said homing peptide selectively binds the alpha 2 chain of collagen IV.
65. The conjugate of claim 60, wherein the peptide portion of said conjugate has a length of less than 50 residues.
66. The conjugate of claim 60, wherein the peptide portion of said conjugate has a length of less than 40 residues.
67. The conjugate of claim 60, wherein the peptide portion of said conjugate has a length of less than 35 residues.
68. The conjugate of claim 60, wherein the peptide portion of said conjugate has a length of less than 30 residues.
69. The conjugate of claim 60, wherein the peptide portion of said conjugate has a length of less than 25 residues.
70. The conjugate of claim 60, wherein the peptide portion of said conjugate has a length of less than 20 residues.
71. The conjugate of claim 60, wherein the peptide portion of said conjugate has a length of less than 15 residues.
72. The conjugate of claim 60, wherein the peptide portion of said conjugate has a length of less than 12 residues.
73. The conjugate of claim 60, wherein the peptide portion of said conjugate has a length of less than 10 residues.
74. The conjugate of claim 60, wherein the peptide portion of said conjugate has a length of less than 9 residues.
75. The conjugate of claim 60, wherein the peptide portion of said conjugate has a length of less than 8 residues.
76. The conjugate of claim 60, wherein the peptide portion of said conjugate has a length of less than 7 residues.
77. The conjugate of claim 60, wherein the peptide portion of said conjugate has a length of less than 6 residues.
78. The conjugate of claim 60, wherein said moiety is a therapeutic agent.
79. The conjugate of claim 78, wherein said therapeutic agent is a cancer chemotherapeutic agent.
80. The conjugate of claim 78, wherein said therapeutic agent is a cytotoxic agent.

81. The conjugate of claim 78, wherein said therapeutic agent is an anti-angiogenic agent.

82. The conjugate of claim 78, wherein said therapeutic agent is a polypeptide.

83. The conjugate of claim 60, wherein said moiety is a small molecule.

84. The conjugate of claim 60, wherein said moiety comprises a virus.

85. The conjugate of claim 84, wherein said virus is a phage.

86. The conjugate of claim 60, comprising at least two homing peptides that each selectively binds collagen.

87. The conjugate of claim 86, wherein said at least two homing peptides each independently comprises the amino acid sequence CREKA (SEQ ID NO: 1).

88. The conjugate of claim 60, comprising at least ten homing peptides that each selectively binds collagen.

89. The conjugate of claim 88, wherein said at least ten homing peptides each independently comprises the amino acid sequence CREKA (SEQ ID NO: 1).

90. The conjugate of claim 60, comprising at least 100 homing peptides that each selectively binds collagen.

91. The conjugate of claim 90, wherein said at least 100 homing peptides each independently comprises the amino acid sequence CREKA (SEQ ID NO: 1).

92. The conjugate of claim 90, wherein said moiety comprises a virus.

93. The conjugate of claim 92, wherein said virus is a phage.

* * * * *

```
                          SEQUENCE LISTING

<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1

Cys Arg Glu Lys Ala
1               5

<210> SEQ ID NO 2
<211> LENGTH: 138
<212> TYPE: PRT
<213> ORGANISM: Mus musculus

<400> SEQUENCE: 2

Gly Glu Arg Gly Glu Gln Gly Pro Pro Gly Pro Ser Val Tyr Ser Pro
1               5                   10                  15

His Pro Ser Leu Ala Lys Gly Ala Arg Gly Asp Pro Gly Phe Gln Gly
            20                  25                  30

Ala His Gly Glu Pro Gly Ser Arg Gly Glu Pro Gly Glu Pro Gly Thr
        35                  40                  45

Ala Gly Pro Pro Gly Pro Ser Val Gly Asp Glu Asp Ser Met Arg Gly
    50                  55                  60

Leu Pro Gly Glu Met Gly Pro Lys Gly Phe Ser Gly Glu Pro Gly Ser
65                  70                  75                  80

Pro Ala Arg Tyr Leu Gly Pro Pro Gly Ala Asp Gly Arg Pro Gly Pro
                85                  90                  95

Gln Gly Val Pro Gly Pro Ala Gly Pro Gly Pro Asp Gly Phe Leu
            100                 105                 110

Phe Gly Leu Lys Gly Ser Glu Gly Arg Val Gly Tyr Pro Gly Pro Ser
        115                 120                 125

Gly Phe Pro Gly Thr Arg Gly Gln Ala Trp
    130                 135

<210> SEQ ID NO 3
<211> LENGTH: 139
<212> TYPE: PRT
<213> ORGANISM: Mus musculus

<400> SEQUENCE: 3

Gly Glu Arg Gly Glu Gln Gly Pro Pro Gly Pro Ser Val Tyr Ser Pro
1               5                   10                  15
```

```
His Pro Ser Leu Ala Lys Gly Ala Arg Gly Asp Pro Gly Phe Gln Gly
            20                  25                  30

Ala His Gly Glu Pro Gly Ser Arg Gly Glu Pro Gly Glu Pro Gly Thr
        35                  40                  45

Ala Gly Pro Pro Gly Pro Ser Val Gly Asp Glu Asp Ser Met Arg Gly
    50                  55                  60

Leu Pro Gly Glu Met Gly Pro Lys Gly Phe Ser Gly Glu Pro Gly Ser
65                  70                  75                  80

Pro Ala Arg Tyr Leu Gly Pro Gly Ala Asp Gly Arg Pro Gly Pro
                85                  90                  95

Gln Gly Val Pro Gly Pro Ala Gly Pro Gly Pro Asp Gly Phe Leu
            100                 105                 110

Phe Gly Leu Lys Gly Ser Glu Gly Arg Val Gly Tyr Pro Gly Pro Ser
            115                 120                 125

Gly Phe Pro Gly Thr Arg Gly Gln Lys Gly Trp
            130                 135

<210> SEQ ID NO 4
<211> LENGTH: 1712
<212> TYPE: PRT
<213> ORGANISM: Homo sapeins

<400> SEQUENCE: 4

Met Gly Arg Asp Gln Arg Ala Val Ala Gly Pro Ala Leu Arg Arg Trp
1               5                   10                  15

Leu Leu Leu Gly Thr Val Thr Val Gly Phe Leu Ala Gln Ser Val Leu
            20                  25                  30

Ala Gly Val Lys Lys Phe Asp Val Pro Cys Gly Gly Arg Asp Cys Ser
        35                  40                  45

Gly Gly Cys Gln Cys Tyr Pro Glu Lys Gly Gly Arg Gly Gln Pro Gly
    50                  55                  60

Pro Val Gly Pro Gln Gly Tyr Asn Gly Pro Pro Gly Leu Gln Gly Phe
65                  70                  75                  80

Pro Gly Leu Gln Gly Arg Lys Gly Asp Lys Gly Glu Arg Gly Ala Pro
                85                  90                  95

Gly Val Thr Gly Pro Lys Gly Asp Val Gly Ala Arg Gly Val Ser Gly
            100                 105                 110

Phe Pro Gly Ala Asp Gly Ile Pro Gly His Pro Gly Gln Gly Gly Pro
            115                 120                 125

Arg Gly Arg Pro Gly Tyr Asp Gly Cys Asn Gly Thr Gln Gly Asp Ser
        130                 135                 140

Gly Pro Gln Gly Pro Gly Ser Glu Gly Phe Thr Gly Pro Pro Gly
145                 150                 155                 160

Pro Gln Gly Pro Lys Gly Gln Lys Gly Glu Pro Tyr Ala Leu Pro Lys
                165                 170                 175

Glu Glu Arg Asp Arg Tyr Arg Gly Glu Pro Gly Glu Pro Gly Leu Val
            180                 185                 190

Gly Phe Gln Gly Pro Pro Gly Arg Pro Gly His Val Gly Gln Met Gly
        195                 200                 205

Pro Val Gly Ala Pro Gly Arg Pro Gly Pro Pro Gly Pro Pro Gly Pro
    210                 215                 220

Lys Gly Gln Gln Gly Asn Arg Gly Leu Gly Phe Tyr Gly Val Lys Gly
225                 230                 235                 240

Glu Lys Gly Asp Val Gly Gln Pro Gly Pro Asn Gly Ile Pro Ser Asp
                245                 250                 255
```

-continued

```
Thr Leu His Pro Ile Ile Ala Pro Thr Gly Val Thr Phe His Pro Asp
            260                 265                 270
Gln Tyr Lys Gly Glu Lys Gly Ser Glu Gly Glu Pro Gly Ile Arg Gly
            275                 280                 285
Ile Ser Leu Lys Gly Glu Glu Gly Ile Met Gly Phe Pro Gly Leu Arg
            290                 295                 300
Gly Tyr Pro Gly Leu Ser Gly Glu Lys Gly Ser Pro Gly Gln Lys Gly
305                 310                 315                 320
Ser Arg Gly Leu Asp Gly Tyr Gln Gly Pro Asp Gly Pro Arg Gly Pro
            325                 330                 335
Lys Gly Glu Ala Gly Asp Pro Gly Pro Pro Gly Leu Pro Ala Tyr Ser
            340                 345                 350
Pro His Pro Ser Leu Ala Lys Gly Ala Arg Gly Asp Pro Gly Phe Pro
            355                 360                 365
Gly Ala Gln Gly Glu Pro Gly Ser Gln Gly Glu Pro Gly Asp Pro Gly
            370                 375                 380
Leu Pro Gly Pro Pro Gly Leu Ser Ile Gly Asp Gly Asp Gln Arg Arg
385                 390                 395                 400
Gly Leu Pro Gly Glu Met Gly Pro Lys Gly Phe Ile Gly Asp Pro Gly
            405                 410                 415
Ile Pro Ala Leu Tyr Gly Gly Pro Pro Gly Pro Asp Gly Lys Arg Gly
            420                 425                 430
Pro Pro Gly Pro Pro Gly Leu Pro Gly Pro Pro Gly Pro Asp Gly Phe
            435                 440                 445
Leu Phe Gly Leu Lys Gly Ala Lys Gly Arg Ala Gly Phe Pro Gly Leu
            450                 455                 460
Pro Gly Ser Pro Gly Ala Pro Gly Pro Lys Gly Trp Lys Gly Asp Ala
465                 470                 475                 480
Gly Glu Cys Arg Cys Thr Glu Gly Asp Glu Ala Ile Lys Gly Leu Pro
            485                 490                 495
Gly Leu Pro Gly Pro Lys Gly Phe Ala Gly Ile Asn Gly Glu Pro Gly
            500                 505                 510
Arg Lys Gly Asp Lys Gly Asp Pro Gly Gln His Gly Leu Pro Gly Phe
            515                 520                 525
Pro Gly Leu Lys Gly Val Pro Gly Asn Ile Gly Ala Pro Gly Pro Lys
            530                 535                 540
Gly Ala Lys Gly Asp Ser Arg Thr Ile Thr Thr Lys Gly Glu Arg Gly
545                 550                 555                 560
Gln Pro Gly Val Pro Gly Val Pro Gly Met Lys Gly Asp Asp Gly Ser
            565                 570                 575
Pro Gly Arg Asp Gly Leu Asp Gly Phe Pro Gly Leu Pro Gly Pro Pro
            580                 585                 590
Gly Asp Gly Ile Lys Gly Pro Pro Gly Asp Pro Gly Tyr Pro Gly Ile
            595                 600                 605
Pro Gly Thr Lys Gly Thr Pro Gly Glu Met Gly Pro Pro Gly Leu Gly
            610                 615                 620
Leu Pro Gly Leu Lys Gly Gln Arg Gly Phe Pro Gly Asp Ala Gly Leu
625                 630                 635                 640
Pro Gly Pro Pro Gly Phe Leu Gly Pro Pro Gly Pro Ala Gly Thr Pro
            645                 650                 655
Gly Gln Ile Asp Cys Asp Thr Asp Val Lys Arg Ala Val Gly Gly Asp
            660                 665                 670
```

```
Arg Gln Glu Ala Ile Gln Pro Gly Cys Ile Gly Gly Pro Lys Gly Leu
            675                 680                 685
Pro Gly Leu Pro Gly Pro Gly Pro Thr Gly Ala Lys Gly Leu Arg
        690                 695                 700
Gly Ile Pro Gly Phe Ala Gly Ala Asp Gly Gly Pro Gly Pro Arg Gly
705                 710                 715                 720
Leu Pro Gly Asp Ala Gly Arg Glu Gly Phe Pro Gly Pro Pro Gly Phe
                725                 730                 735
Ile Gly Pro Arg Gly Ser Lys Gly Ala Val Gly Leu Pro Gly Pro Asp
            740                 745                 750
Gly Ser Pro Gly Pro Ile Gly Leu Pro Gly Pro Asp Gly Pro Pro Gly
        755                 760                 765
Glu Arg Gly Leu Pro Gly Glu Val Leu Gly Ala Gln Pro Gly Pro Arg
    770                 775                 780
Gly Asp Ala Gly Val Pro Gly Gln Pro Gly Leu Lys Gly Leu Pro Gly
785                 790                 795                 800
Asp Arg Gly Pro Pro Gly Phe Arg Gly Ser Gln Gly Met Pro Gly Met
                805                 810                 815
Pro Gly Leu Lys Gly Gln Pro Gly Leu Pro Gly Pro Ser Gly Gln Pro
            820                 825                 830
Gly Leu Tyr Gly Pro Pro Gly Leu His Gly Phe Pro Gly Ala Pro Gly
        835                 840                 845
Gln Glu Gly Pro Leu Gly Leu Pro Gly Ile Pro Gly Arg Glu Gly Leu
    850                 855                 860
Pro Gly Asp Arg Gly Asp Pro Gly Asp Thr Gly Ala Pro Gly Pro Val
865                 870                 875                 880
Gly Met Lys Gly Leu Ser Gly Asp Arg Gly Asp Ala Gly Phe Thr Gly
                885                 890                 895
Glu Gln Gly His Pro Gly Ser Pro Gly Phe Lys Gly Ile Asp Gly Met
            900                 905                 910
Pro Gly Thr Pro Gly Leu Lys Gly Asp Arg Gly Ser Pro Gly Met Asp
        915                 920                 925
Gly Phe Gln Gly Met Pro Gly Leu Lys Gly Arg Pro Gly Phe Pro Gly
    930                 935                 940
Ser Lys Gly Glu Ala Gly Phe Phe Gly Ile Pro Gly Leu Lys Gly Leu
945                 950                 955                 960
Ala Gly Glu Pro Gly Phe Lys Gly Ser Arg Gly Asp Pro Gly Pro Pro
                965                 970                 975
Gly Pro Pro Pro Val Ile Leu Pro Gly Met Lys Asp Ile Lys Gly Glu
            980                 985                 990
Lys Gly Asp Glu Gly Pro Met Gly Leu Lys Gly Tyr Leu Gly Ala Lys
        995                 1000                1005
Gly Ile Gln Gly Met Pro Gly Ile Pro Gly Leu Ser Gly Ile Pro Gly
    1010                1015                1020
Leu Pro Gly Arg Pro Gly His Ile Lys Gly Val Lys Gly Asp Ile Gly
1025                1030                1035                1040
Val Pro Gly Ile Pro Gly Leu Pro Gly Phe Pro Gly Val Ala Gly Pro
                1045                1050                1055
Pro Gly Ile Thr Gly Phe Pro Gly Phe Ile Gly Ser Arg Gly Asp Lys
            1060                1065                1070
Gly Ala Pro Gly Arg Ala Gly Leu Tyr Gly Glu Ile Gly Ala Thr Gly
        1075                1080                1085
Asp Phe Gly Asp Ile Gly Asp Thr Ile Asn Leu Pro Gly Arg Pro Gly
```

-continued

```
            1090                1095                1100
Leu Lys Gly Glu Arg Gly Thr Thr Gly Ile Pro Gly Leu Lys Gly Phe
1105                1110                1115                1120

Phe Gly Glu Lys Gly Thr Glu Gly Asp Ile Gly Phe Pro Gly Ile Thr
                1125                1130                1135

Gly Val Thr Gly Val Gln Gly Pro Pro Gly Leu Lys Gly Gln Thr Gly
                1140                1145                1150

Phe Pro Gly Leu Thr Gly Pro Pro Gly Ser Gln Gly Glu Leu Gly Arg
                1155                1160                1165

Ile Gly Leu Pro Gly Gly Lys Gly Asp Asp Gly Trp Pro Gly Ala Pro
            1170                1175                1180

Gly Leu Pro Gly Phe Pro Gly Leu Arg Gly Ile Arg Gly Leu His Gly
1185                1190                1195                1200

Leu Pro Gly Thr Lys Gly Phe Pro Gly Ser Pro Gly Ser Asp Ile His
                1205                1210                1215

Gly Asp Pro Gly Phe Pro Gly Pro Pro Gly Glu Arg Gly Asp Pro Gly
                1220                1225                1230

Glu Ala Asn Thr Leu Pro Gly Pro Val Gly Val Pro Gly Gln Lys Gly
                1235                1240                1245

Asp Gln Gly Ala Pro Gly Glu Arg Gly Pro Pro Gly Ser Pro Gly Leu
            1250                1255                1260

Gln Gly Phe Pro Gly Ile Thr Pro Pro Ser Asn Ile Ser Gly Ala Pro
1265                1270                1275                1280

Gly Asp Lys Gly Ala Pro Gly Ile Phe Gly Leu Lys Gly Tyr Arg Gly
                1285                1290                1295

Pro Pro Gly Pro Pro Gly Ser Ala Ala Leu Pro Gly Ser Lys Gly Asp
                1300                1305                1310

Thr Gly Asn Pro Gly Ala Pro Gly Thr Pro Gly Thr Lys Gly Trp Ala
                1315                1320                1325

Gly Asp Ser Gly Pro Gln Gly Arg Pro Gly Val Phe Gly Leu Pro Gly
            1330                1335                1340

Glu Lys Gly Pro Arg Gly Glu Gln Gly Phe Met Gly Asn Thr Gly Pro
1345                1350                1355                1360

Thr Gly Ala Val Gly Asp Arg Gly Pro Lys Gly Pro Lys Gly Asp Pro
                1365                1370                1375

Gly Phe Pro Gly Ala Pro Gly Thr Val Gly Ala Pro Gly Ile Ala Gly
                1380                1385                1390

Ile Pro Gln Lys Ile Ala Val Gln Pro Gly Thr Val Gly Pro Gln Gly
            1395                1400                1405

Arg Arg Gly Pro Pro Gly Ala Pro Gly Glu Met Gly Pro Gln Gly Pro
1410                1415                1420

Pro Gly Glu Pro Gly Phe Arg Gly Ala Pro Gly Lys Ala Gly Pro Gln
1425                1430                1435                1440

Gly Arg Gly Gly Val Ser Ala Val Pro Gly Phe Arg Gly Asp Glu Gly
                1445                1450                1455

Pro Ile Gly His Gln Gly Pro Ile Gly Gln Glu Gly Ala Pro Gly Arg
                1460                1465                1470

Pro Gly Ser Pro Gly Leu Pro Gly Met Pro Gly Arg Ser Val Ser Ile
            1475                1480                1485

Gly Tyr Leu Leu Val Lys His Ser Gln Thr Asp Gln Glu Pro Met Cys
            1490                1495                1500

Pro Val Gly Met Asn Lys Leu Trp Ser Gly Tyr Ser Leu Leu Tyr Phe
1505                1510                1515                1520
```

```
Glu Gly Gln Glu Lys Ala His Asn Gln Asp Leu Gly Leu Ala Gly Ser
            1525                1530                1535

Cys Leu Ala Arg Phe Ser Thr Met Pro Phe Leu Tyr Cys Asn Pro Gly
        1540                1545                1550

Asp Val Cys Tyr Tyr Ala Ser Arg Asn Asp Lys Ser Tyr Trp Leu Ser
        1555                1560                1565

Thr Thr Ala Pro Leu Pro Met Met Pro Val Ala Glu Asp Glu Ile Lys
        1570                1575                1580

Pro Tyr Ile Ser Arg Cys Ser Val Cys Glu Ala Pro Ala Ile Ala Ile
1585                1590                1595                1600

Ala Val His Ser Gln Asp Val Ser Ile Pro His Cys Pro Ala Gly Trp
            1605                1610                1615

Arg Ser Leu Trp Ile Gly Tyr Ser Phe Leu Met His Thr Ala Ala Gly
            1620                1625                1630

Asp Glu Gly Gly Gly Gln Ser Leu Val Ser Pro Gly Ser Cys Leu Glu
            1635                1640                1645

Asp Phe Arg Ala Thr Pro Phe Ile Glu Cys Asn Gly Gly Arg Gly Thr
            1650                1655                1660

Cys His Tyr Tyr Ala Asn Lys Tyr Ser Phe Trp Leu Thr Thr Ile Pro
1665                1670                1675                1680

Glu Gln Ser Phe Gln Gly Ser Pro Ser Ala Asp Thr Leu Lys Ala Gly
            1685                1690                1695

Leu Ile Arg Thr His Ile Ser Arg Cys Gln Val Cys Met Lys Asn Leu
            1700                1705                1710

<210> SEQ ID NO 5
<211> LENGTH: 5
<212> TYPE: PRT
<213> ORGANISM: Artificial Sequence
<220> FEATURE:
<223> OTHER INFORMATION: synthetic construct

<400> SEQUENCE: 5

Ser Arg Glu Lys Ala
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic construct

<400> SEQUENCE: 6

Cys Lys Glu Lys Ala
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic construct

<400> SEQUENCE: 7

Cys Arg Asp Lys Ala
1               5

<210> SEQ ID NO 8
<211> LENGTH: 5
```

```
<212> TYPE: PRT
<213> ORGANISM: Artificial Sequence
<220> FEATURE:
<223> OTHER INFORMATION: synthetic construct

<400> SEQUENCE: 8

Cys Arg Glu Arg Ala
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic construct

<400> SEQUENCE: 9

Cys Arg Glu Lys Val
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic construct

<400> SEQUENCE: 10

Ser Lys Glu Lys Ala
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic construct

<400> SEQUENCE: 11

Ser Arg Asp Lys Ala
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic construct

<400> SEQUENCE: 12

Ser Arg Glu Arg Ala
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic construct

<400> SEQUENCE: 13

Ser Arg Glu Lys Val
1               5

<210> SEQ ID NO 14
<211> LENGTH: 5
<212> TYPE: PRT
```

-continued

```
<213> ORGANISM: Artificial Sequence
<220> FEATURE:
<223> OTHER INFORMATION: synthetic construct

<400> SEQUENCE: 14

Cys Lys Asp Lys Ala
 1               5

<210> SEQ ID NO 15
<211> LENGTH: 5
<212> TYPE: PRT
<213> ORGANISM: Artificial Sequence
<220> FEATURE:
<223> OTHER INFORMATION: synthetic construct

<400> SEQUENCE: 15

Cys Lys Glu Arg Ala
 1               5

<210> SEQ ID NO 16
<211> LENGTH: 5
<212> TYPE: PRT
<213> ORGANISM: Artificial Sequence
<220> FEATURE:
<223> OTHER INFORMATION: synthetic construct

<400> SEQUENCE: 16

Cys Lys Glu Lys Val
 1               5

<210> SEQ ID NO 17
<211> LENGTH: 5
<212> TYPE: PRT
<213> ORGANISM: Artificial Sequence
<220> FEATURE:
<223> OTHER INFORMATION: synthetic construct

<400> SEQUENCE: 17

Cys Arg Asp Arg Ala
 1               5

<210> SEQ ID NO 18
<211> LENGTH: 5
<212> TYPE: PRT
<213> ORGANISM: Artificial Sequence
<220> FEATURE:
<223> OTHER INFORMATION: synthetic construct

<400> SEQUENCE: 18

Cys Arg Asp Lys Val
 1               5

<210> SEQ ID NO 19
<211> LENGTH: 5
<212> TYPE: PRT
<213> ORGANISM: Artificial Sequence
<220> FEATURE:
<223> OTHER INFORMATION: synthetic construct

<400> SEQUENCE: 19

Cys Arg Glu Arg Val
 1               5

<210> SEQ ID NO 20
<211> LENGTH: 14
<212> TYPE: PRT
<213> ORGANISM: Artificial Sequence
```

```
<220> FEATURE:
<223> OTHER INFORMATION: synthetic construct

<400> SEQUENCE: 20

Lys Leu Ala Lys Leu Ala Lys Lys Leu Ala Lys Leu Ala Lys
 1               5                   10

<210> SEQ ID NO 21
<211> LENGTH: 14
<212> TYPE: PRT
<213> ORGANISM: Artificial Sequence
<220> FEATURE:
<223> OTHER INFORMATION: synthetic construct

<400> SEQUENCE: 21

Lys Leu Ala Lys Lys Leu Ala Lys Leu Ala Lys Lys Leu Ala
 1               5                   10

<210> SEQ ID NO 22
<211> LENGTH: 14
<212> TYPE: PRT
<213> ORGANISM: Artificial Sequence
<220> FEATURE:
<223> OTHER INFORMATION: synthetic construct

<400> SEQUENCE: 22

Lys Ala Ala Lys Lys Ala Ala Lys Ala Ala Lys Lys Ala Ala
 1               5                   10

<210> SEQ ID NO 23
<211> LENGTH: 21
<212> TYPE: PRT
<213> ORGANISM: Artificial Sequence
<220> FEATURE:
<223> OTHER INFORMATION: synthetic construct

<400> SEQUENCE: 23

Lys Leu Gly Lys Lys Leu Gly Lys Leu Gly Lys Lys Leu Gly Lys Leu
 1               5                   10                  15

Gly Lys Lys Leu Gly
                20
```